United States Patent
Stoessel et al.

(10) Patent No.: US 9,627,626 B2
(45) Date of Patent: Apr. 18, 2017

(54) COMPOUNDS FOR ORGANIC ELECTROLUMINESCENT DEVICES

(75) Inventors: Philipp Stoessel, Frankfurt am Main (DE); Arne Buesing, Frankfurt am Main (DE); Esther Breuning, Ober-Ramstadt (DE); Christof Pflumm, Darmstadt (DE); Amir Hossain, Frankfurt am Main (DE); Thomas Eberle, Landau (DE); Teresa Mujica-Fernaud, Darmstadt (DE)

(73) Assignee: Merck Patent GmbH (DE)

( * ) Notice: Subject to any disclaimer, the term of this patent is extended or adjusted under 35 U.S.C. 154(b) by 690 days.

(21) Appl. No.: 13/979,545

(22) PCT Filed: Dec. 15, 2011

(86) PCT No.: PCT/EP2011/006355
§ 371 (c)(1),
(2), (4) Date: Jul. 12, 2013

(87) PCT Pub. No.: WO2012/095143
PCT Pub. Date: Jul. 19, 2012

(65) Prior Publication Data
US 2013/0285036 A1    Oct. 31, 2013

(30) Foreign Application Priority Data

Jan. 13, 2011 (EP) .................................. 11000214

(51) Int. Cl.
| | | |
|---|---|---|
| *H01L 51/54* | (2006.01) | |
| *C09K 11/06* | (2006.01) | |
| *H01L 51/00* | (2006.01) | |
| *C07D 487/22* | (2006.01) | |
| *C09B 57/00* | (2006.01) | |
| *H01L 51/50* | (2006.01) | |

(52) U.S. Cl.
CPC ........ *H01L 51/0072* (2013.01); *C07D 487/22* (2013.01); *C09B 57/00* (2013.01); *H01L 51/0067* (2013.01); *H01L 51/5088* (2013.01)

(58) Field of Classification Search
None
See application file for complete search history.

(56) References Cited

U.S. PATENT DOCUMENTS

| 7,538,341 B2 | 5/2009 | Son et al. |
| 2009/0066237 A1* | 3/2009 | Kambe ............... H01L 51/5218 313/504 |
| 2009/0115316 A1 | 5/2009 | Zheng et al. |
| 2010/0109843 A1 | 5/2010 | Sugaya |
| 2010/0301316 A1 | 12/2010 | Nowatari et al. |

FOREIGN PATENT DOCUMENTS

| JP | 2003-519432 A | 6/2003 |
| JP | 2007-230974 A | 9/2007 |
| JP | 2010-114961 A | 5/2010 |
| JP | 2011243764 A | 12/2011 |
| WO | WO-01/49806 A1 | 7/2001 |

OTHER PUBLICATIONS

Machine translation of JP2007-230974. Date of publication: Sep. 13, 2007.*
Barton et al., "Formation of a Tribenzo[12]Annulene by Thermolysis of a Benzotricinnoline. A Unique [2 + 2 + 2] Benzene—Acetylene Cycloreversion?" *Tetrahedron Letters*, vol. 25, No. 43, pp. 4967-4970 (1984).
International Search Report for PCT/EP2011/006355 mailed Mar. 14, 2012.

* cited by examiner

*Primary Examiner* — Andrew K Bohaty
(74) *Attorney, Agent, or Firm* — Drinker Biddle & Reath LLP

(57) ABSTRACT

The present invention relates to aromatic nitrogen heterocycles, and to electronic devices, in particular organic electroluminescent devices, which comprise these aromatic nitrogen heterocycles, in particular in a hole-injection layer and/or in a hole-transport layer and/or in a hole-blocking layer and/or in an electron-transport layer and/or in an emitting layer.

13 Claims, No Drawings

COMPOUNDS FOR ORGANIC ELECTROLUMINESCENT DEVICES

CROSS-REFERENCE TO RELATED APPLICATIONS

This application is a national stage application (under 35 U.S.C. §371) of PCT/EP2011/006355, filed Dec. 15, 2011, which claims benefit of European application 11000214.4, filed Jan. 13, 2011.

The present invention relates to novel compounds which contain aromatic nitrogen heterocycles, for use in electronic devices, in particular in organic electroluminescent devices.

The structure of organic electroluminescent devices (OLEDs) in which organic semiconductors are employed as functional materials is described, for example, in U.S. Pat. Nos. 4,539,507, 5,151,629, EP 0676461 and WO 98/27136. However, further improvements are still desirable in order to use these devices for high-quality displays with a long lifetime. Thus, there is currently still a need for improvement, in particular, in the lifetime, the efficiency and the operating voltage of organic electroluminescent devices. Furthermore, it is necessary for the compounds to have high thermal stability and to be sublimable without decomposition.

Improvements are still desirable, in particular, in the charge-injection and -transport materials since it is precisely the properties of the charge-transport materials that also have a significant influence on the above-mentioned properties of the organic electroluminescent device. In particular, there is a need for improvement in electron-transport materials and hole-injection or hole-transport materials which simultaneously result in good efficiency, a long lifetime and a low operating voltage. The properties of these materials, in particular, are frequently also limiting for the lifetime, the efficiency and the operating voltage of the organic electroluminescent device.

Besides triarylamine derivatives or carbazole derivatives, the hole-injection or hole-transport materials used in organic electroluminescent devices in accordance with the prior art are, in particular, also hexaazatriphenylene derivatives, in particular those which are substituted by cyano groups (for example WO 2001/049806). These compounds are generally used as a separate layer which is adjacent to one or more hole-transport layers or in a mixture with a hole-transport material. On use of these compounds, there is still a need for improvement with respect to the lifetime, the efficiency and the operating voltage. Furthermore, it would be desirable to have materials which have a higher triplet level available for use in combination with triplet emitters.

$AlQ_3$ has already been used for some time as electron-transport material (for example U.S. Pat. No. 4,539,507), but has a number of disadvantages: it cannot be vapour-deposited without a residue since it partially decomposes at the sublimation temperature, which represents a major problem, in particular, for production plants. This has the consequence that the vapour-deposition sources must repeatedly be cleaned or changed. Furthermore, decomposition products of $AlQ_3$ reach the OLED, where they contribute to a shortened lifetime and reduced quantum and power efficiency. In addition, $AlQ_3$ has low electron mobility, which results in higher voltages and thus in lower power efficiency. In order to avoid short circuits in the display, it would be desirable to increase the layer thickness; this is not possible with $AlQ_3$ owing to the low charge-carrier mobility and the resultant increase in voltage. The charge-carrier mobility of other electron conductors (U.S. Pat. No. 4,539,507) is likewise too low to build up thicker layers therewith, with the lifetime of the OLED being even worse than on use of $AlQ_3$. The inherent colour (yellow in the solid state) of $AlQ_3$ also proves to be unfavourable, possibly resulting in colour shifts due to reabsorption and weak re-emission, especially in the case of blue OLEDs. Blue OLEDs can only be produced here with considerable adverse effects on efficiency and colour location.

Thus, there continues to be a demand for electron-transport materials and hole-injection and hole-transport materials which result in good efficiencies and at the same time in long lifetimes in organic electroluminescent devices. Surprisingly, it has now been found that organic electroluminescent devices which comprise certain nitrogen heteroaromatic compounds—indicated below—as electron-transport materials or as hole-injection or hole-transport materials have very good properties, in particular in relation to efficiency and lifetime and in particular also in combination with triplet emitters. In particular, better results are obtained with these materials than with the hexaazatriphenylene derivatives in accordance with the prior art.

The invention relates to a compound of the following formula (1),

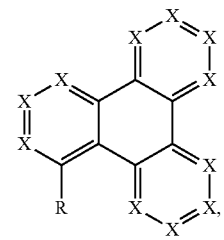

formula (1)

where the following applies to the symbols used:

X is on each occurrence, identically or differently, CR or N, with the proviso that two symbols X in each ring stand for N and the remaining symbols X stand for CR;

R is on each occurrence, identically or differently, H, D, F, Cl, Br, I, CHO, $N(R^1)_2$, $N(Ar)_2$, $C(=O)R^1$, $C(=O)Ar$, $P(=O)(R^1)_2$, $P(=O)(Ar)_2$, $S(=O)Ar$, $S(=O)_2Ar$, $CR^1=CR^1Ar$, CN, $NO_2$, $Si(R^1)_3$, $B(OR^1)_2$, $B(R^1)_2$, $B(Ar)_2$, $B(N(R^1)_2)_2$, $P(R^1)_2$, $OSO_2R^1$, COOH, $COOR^1$, a straight-chain alkyl, alkoxy or thioalkoxy group having 1 to 40 C atoms or a straight-chain alkenyl or alkynyl group having 2 to 40 C atoms or a branched or cyclic alkyl, alkenyl, alkynyl, alkoxy or thioalkoxy group having 3 to 40 C atoms, each of which may be substituted by one or more radicals $R^1$, where one or more non-adjacent $CH_2$ groups may be replaced by $R^1C=CR^1$, $C≡C$, $Si(R^1)_2$, $Ge(R^1)_2$, $Sn(R^1)_2$, C=O, C=S, C=Se, $C=NR^1$, $P(=O)(R^1)$, SO, $SO_2$, $NR^1$, O, S or $CONR^1$ and where one or more H atoms may be replaced by D, F, Cl, Br, I, CN or $NO_2$, or an aromatic or heteroaromatic ring system having 5 to 60 aromatic ring atoms, which may in each case be substituted by one or more radicals $R^1$, or an aryloxy or heteroaryloxy group having 5 to 60 aromatic ring atoms, which may in each case be substituted by one or more radicals $R^1$, or a combination of these systems; two adjacent radicals R here may in each case form a mono- or polycyclic, aliphatic, aromatic or heteroaromatic ring system with one another;

$R^1$ is on each occurrence, identically or differently, H, D, F, Cl, Br, I, CHO, $N(R^2)_2$, $N(Ar)_2$, $C(=O)Ar$, $P(=O)(Ar)_2$, $S(=O)Ar$, $S(=O)_2Ar$, $CR^2=CR^2Ar$, CN, $NO_2$, $Si(R^2)_3$, B(OR$^2$)$_2$, B(R$^2$)$_2$, B(N(R$^2$)$_2$)$_2$, OSO$_2$R$^2$, a straight-chain alkyl, alkoxy or thioalkoxy group having 1 to 40 C atoms or a straight-chain alkenyl or alkynyl group having 2 to 40 C atoms or a branched or cyclic alkyl, alkenyl, alkynyl, alkoxy or thioalkoxy group having 3 to 40 C atoms, each of which may be substituted by one or more radicals R$^2$, where one or more non-adjacent CH$_2$ groups may be replaced by R$^2$C=CR$^2$, C≡C, Si(R$^2$)$_2$, Ge(R$^2$)$_2$, Sn(R$^2$)$_2$, C=O, C=S, C=Se, C=NR$^2$, P(=O)(R$^2$), SO, SO$_2$, NR$^2$, O, S or CONR$^2$ and where one or more H atoms may be replaced by D, F, Cl, Br, I, CN or NO$_2$, or an aromatic or heteroaromatic ring system having 5 to 60 aromatic ring atoms, which may in each case be substituted by one or more radicals R$^2$, or an aryloxy or heteroaryloxy group having 5 to 60 aromatic ring atoms, which may be substituted by one or more radicals R$^2$, or a combination of these systems;

Ar is on each occurrence, identically or differently, an aromatic or heteroaromatic ring system having 5 to 30 aromatic ring atoms, which may be substituted by one or more non-aromatic radicals R$^1$; two radicals Ar which are bonded to the same nitrogen or phosphorus atom may also be linked to one another here by a single bond or a bridge selected from B(R$^2$), C(R$^2$)$_2$, Si(R$^2$)$_2$, C=O, C=NR$^2$, C=C(R$^2$)$_2$, O, S, S=O, SO$_2$, N(R$^2$), P(R$^2$) and P(=O)R$^2$;

R$^2$ is on each occurrence, identically or differently, H, D or an aliphatic, aromatic and/or heteroaromatic hydrocarbon radical having 1 to 20 C atoms, in which, in addition, H atoms may be replaced by F; two or more adjacent substituents R$^2$ here may also form a mono- or polycyclic, aliphatic or aromatic ring system with one another;

the following compound is excluded from the invention:

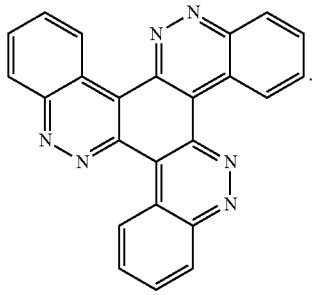 [SMILES: c1ccc2c(c1)nnc1c2c2nnc3ccccc3c2c2nnc3ccccc3c12]

In the sense of the present invention, adjacent radicals R, which can form a further ring with one another, are taken to mean two radicals R which are bonded to directly to adjacent C atoms on the same heterocycle.

An aryl group in the sense of this invention contains 6 to 60 C atoms; a heteroaryl group in the sense of this invention contains 2 to 60 C atoms and at least one heteroatom, with the proviso that the sum of C atoms and heteroatoms is at least 5. The heteroatoms are preferably selected from N, O and/or S. An aryl group or heteroaryl group here is taken to mean either a simple aromatic ring, i.e. benzene, or a simple heteroaromatic ring, for example pyridine, pyrimidine, thiophene, etc., or a condensed aryl or heteroaryl group, for example naphthalene, anthracene, pyrene, quinoline, isoquinoline, etc.

An aromatic ring system in the sense of this invention contains 6 to 60 C atoms in the ring system. A heteroaromatic ring system in the sense of this invention contains 2 to 60 C atoms and at least one heteroatom in the ring system, with the proviso that the sum of C atoms and heteroatoms is at least 5. The heteroatoms are preferably selected from N, O and/or S. In the sense of this invention, an aromatic or heteroaromatic ring system is intended to be taken to mean a system which does not necessarily contain only aryl or heteroaryl groups, but instead in which, in addition, a plurality of aryl or heteroaryl groups may be interrupted by a short non-aromatic unit, such as, for example, a C, N or O atom. Thus, for example, systems such as 9,9'-spirobifluorene, 9,9-diarylfluorene, triarylamine, diaryl ether, stilbene, benzophenone, etc., are also intended to be taken to be aromatic ring systems in the sense of this invention. An aromatic or heteroaromatic ring system is likewise taken to mean systems in which a plurality of aryl or heteroaryl groups are linked to one another by single bonds, for example biphenyl, terphenyl or bipyridine.

For the purposes of the present invention, a $C_1$- to $C_{40}$-alkyl group, in which, in addition, individual H atoms or CH$_2$ groups may be substituted by the above-mentioned groups, is particularly preferably taken to mean the radicals methyl, ethyl, n-propyl, i-propyl, n-butyl, i-butyl, s-butyl, t-butyl, 2-methylbutyl, n-pentyl, s-pentyl, cyclopentyl, n-hexyl, cyclohexyl, n-heptyl, cycloheptyl, n-octyl, cyclooctyl, 2-ethylhexyl, trifluoromethyl, pentafluoroethyl and 2,2,2-trifluoroethyl. An alkenyl group in the sense of this invention is taken to mean, in particular, ethenyl, propenyl, butenyl, pentenyl, cyclopentenyl, hexenyl, cyclohexenyl, heptenyl, cycloheptenyl, octenyl and cyclooctenyl. An alkynyl group in the sense of this invention is taken to mean, in particular, ethynyl, propynyl, butynyl, pentynyl, hexynyl, heptynyl or octynyl. A $C_1$- to $C_{40}$-alkoxy group is particularly preferably taken to mean methoxy, trifluoromethoxy, ethoxy, n-propoxy, i-propoxy, n-butoxy, i-butoxy, s-butoxy, t-butoxy or 2-methylbutoxy. An aromatic or heteroaromatic ring system having 5-60 aromatic ring atoms, which may also in each case be substituted by the above-mentioned radicals R and which may be linked to the aromatic or heteroaromatic ring system via any desired positions, is taken to mean, in particular, groups derived from benzene, naphthalene, anthracene, phenanthrene, benzanthracene, benzophenanthrene, pyrene, chrysene, perylene, fluoroanthene, naphthacene, pentacene, benzopyrene, biphenyl, biphenylene, terphenyl, terphenylene, fluorene, spirobifluorene, dihydrophenanthrene, dihydropyrene, tetrahydropyrene, cis- or trans-indenofluorene, truxene, isotruxene, spirotruxene, spiroisotruxene, furan, benzofuran, isobenzofuran, dibenzofuran, thiophene, benzothiophene, isobenzothiophene, dibenzothiophene, pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, 1,5-diazaanthracene, 2,7-diazapyrene, 2,3-diazapyrene, 1,6-diazapyrene, 1,8-diazapyrene, 4,5-diazapyrene, 4,5,9,10-tetraazaperylene, pyrazine, phenazine, phenoxazine, phenothiazine, fluorubin, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2, 4-triazine, 1,2,3-triazine, tetrazole, 1,2,4,5-tetrazine, 1,2,3,4-tetrazine, 1,2,3,5-tetrazine, purine, pteridine, indolizine and benzothiadiazole.

As described above, the compounds of the formula (1) according to the invention are nitrogen heteroaromatic compounds which have three heteroaromatic condensed part-rings. For a more accurate description of these heteroaromatic part-rings, these are denoted below as heterocycle A, heterocycle B and heterocycle C in the following scheme:

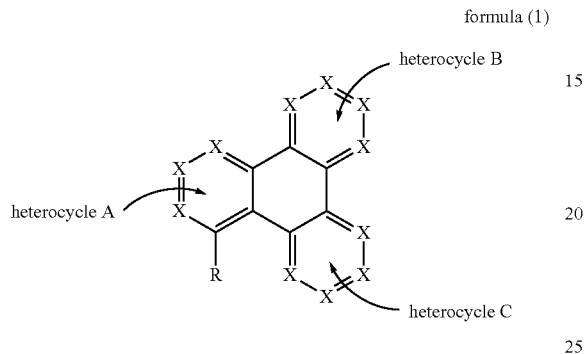

formula (1)

In a preferred embodiment, heterocycle A is selected from the structures of the following formulae (A-1) to (A-3),

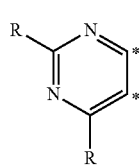

formula (A-1)

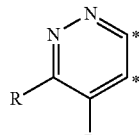

formula (A-2)

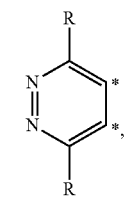

formula (A-3)

where the symbols used have the meanings given above and * denotes the atoms to which heterocycle A is linked in the compound of the formula (1).

In a further preferred embodiment of the invention, heterocycle B is selected from the structures of the following formulae (B-1) to (B-6),

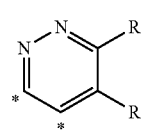

formula (B-1)

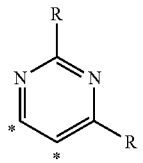

formula (B-2)

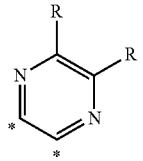

formula (B-3)

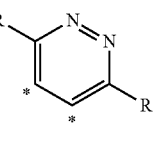

formula (B-4)

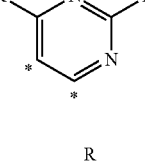

formula (B-5)

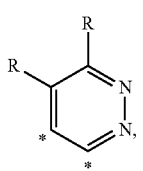

formula (B-6)

where the symbols used have the meanings given above and * denotes the atoms to which heterocycle B is linked in the compound of the formula (1).

In a further preferred embodiment of the invention, heterocycle C is selected from the structures of the following formulae (C-1) to (C-6),

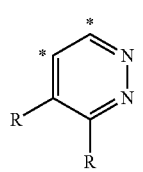

formula (C-1)

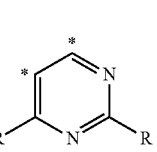

formula (C-2)

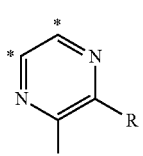

formula (C-3)

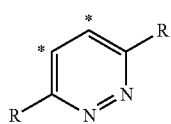
formula (C-4)

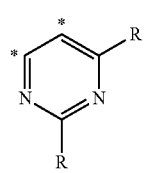
formula (C-5)

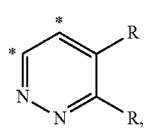
formula (C-6)

where the symbols used have the meanings given above and * denotes the atoms to which heterocycle C is linked in the compound of the formula (1).

Heterocycles (A-1) to (A-3), (B-1) to (B-6) and (C-1) to (C-6) can be combined with one another as desired.

Preferred embodiments of the compounds of the formula (1) are the compounds of the following formulae (2) to (14),

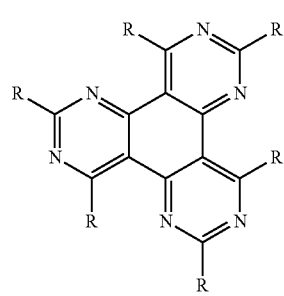
formula (2)

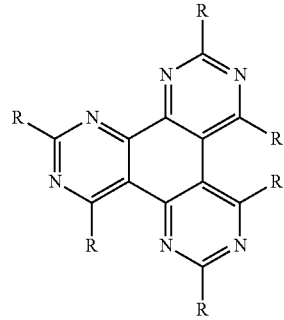
formula (3)

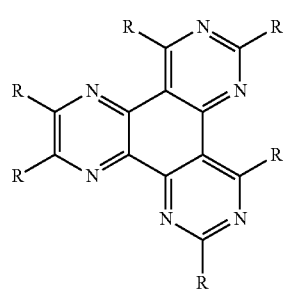
formula (4)

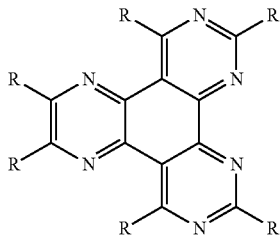
formula (5)

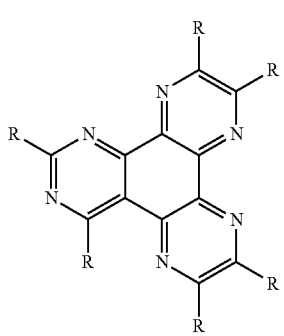
formula (6)

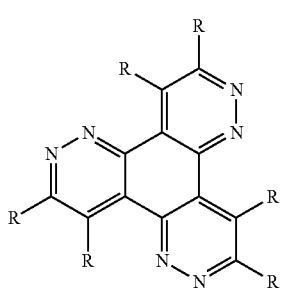
formula (7)

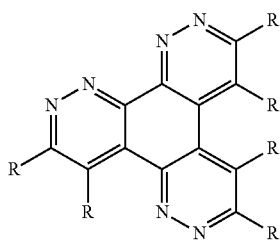
formula (8)

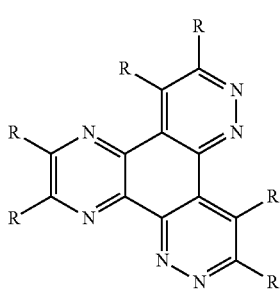
formula (9)

-continued formula (10)
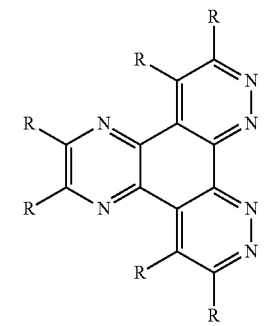

formula (11)
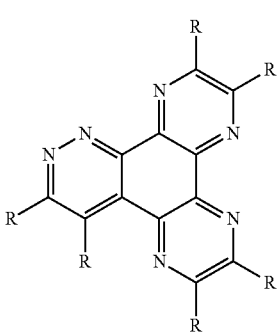

formula (12)
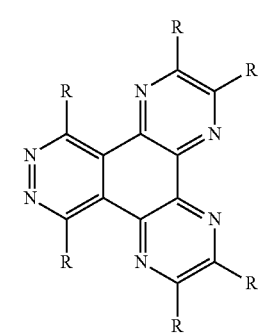

formula (13)
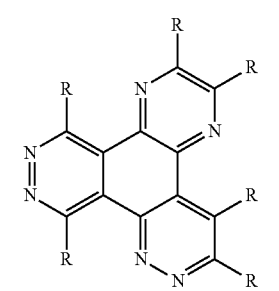

formula (14)
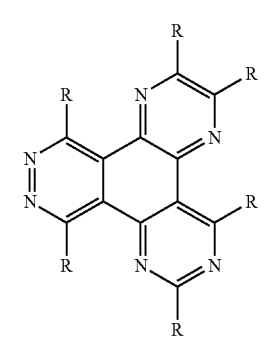

where the symbols used have the meanings given above.

Preference is given to compounds of the formula (1) in which the heteroaromatic skeleton, i.e. the heteroaromatic compound without the radicals R, has $C_{3h}$ or $C_{2v}$ symmetry. Of the compounds mentioned above, the compounds of the formulae (2) and (7) have $C_{3h}$ symmetry, and the compounds of the formulae (5), (10) and (12) have $C_{2v}$ symmetry. These compounds are thus preferred. Very particular preference is given to compounds having $C_{3h}$ symmetry, i.e. compounds of the formulae (2) and (7).

In a preferred embodiment of the invention, R in the compounds of the formulae (1) to (14) and in the moieties of the formulae (A-1) to (A-3), (B-1) to (B-6) and (C-1) to (C-6) stands, identically or differently on each occurrence, for H, F, C(=O)Ar, P(=O)(Ar)$_2$, CN, a straight-chain alkyl group having 1 to 10 C atoms or a branched or cyclic alkyl group having 3 to 10 C atoms, each of which may be substituted by one or more radicals $R^1$, where one or more H atoms may be replaced by F or CN, or an aromatic or heteroaromatic ring system having 5 to 40 aromatic ring atoms, which may in each case be substituted by one or more radicals $R^1$. In a particularly preferred embodiment of the invention, R in the compounds of the formulae (1) to (14) and in the moieties of the formulae (A-1) to (A-3), (B-1) to (B-6) and (C-1) to (C-6) stands, identically or differently on each occurrence, for H, F, CN, $CF_3$, or an aromatic or heteroaromatic ring system having 5 to 30 aromatic ring atoms, which may in each case be substituted by one or more radicals $R^1$, but is preferably unsubstituted. If R stands for an aromatic or heteroaromatic ring system, R is preferably selected from the group consisting of phenyl, 2-, 3- or 4-pyridyl, pyrazinyl, 2-, 4- or 5-pyrimidinyl, 3- or 4-pyridazinyl, triazinyl, ortho-, meta- or para-biphenyl, ortho-, meta- or para-terphenyl, quaterphenyl, 2-fluorenyl, 2-spirobifluorenyl, 1-naphthyl, 2-naphthyl, anthracenyl, phenylanthracenyl, 1- or 2-naphthylanthracenyl, binaphthyl, pyrenyl, fluoranthenyl, 2-, 3-, 4-, 5-, 6- or 7-benzanthracenyl, N-imidazolyl, N-benzimidazolyl, phenyl-N-benzimidazolyl, N-phenylbenzimidazolyl, phenyl-N-phenylbenzimidazolyl or combinations of these groups, each of which may be substituted by one or more radicals $R^1$. In a very particularly preferred embodiment of the invention, R is equal to CN.

In a preferred embodiment of the invention, all radicals R are selected identically. This preference is based on the better synthetic accessibility of the compounds.

In a further preferred embodiment of the invention, at least two radicals R are different from one another, which results in compounds having reduced symmetry. The reduction in symmetry may result in advantages with respect to reduced crystallinity of the compounds. Furthermore, asymmetrical compounds frequently have the advantage that they have a lower vapour-deposition temperature.

Examples of preferred compounds according to the invention are structures (1) to (44) depicted below.

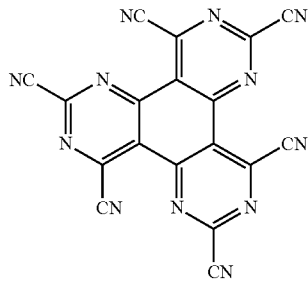
(1)

-continued
(2)
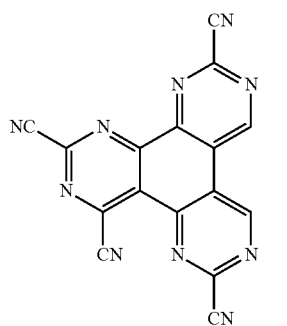
(3)
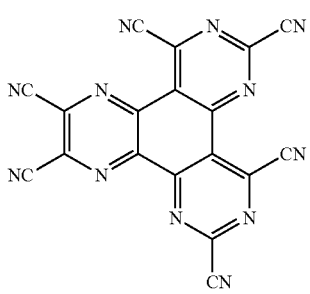
(3)
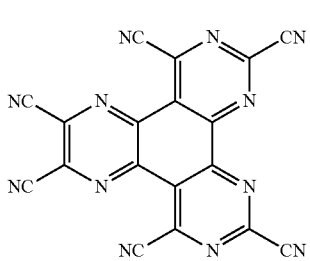
(4)
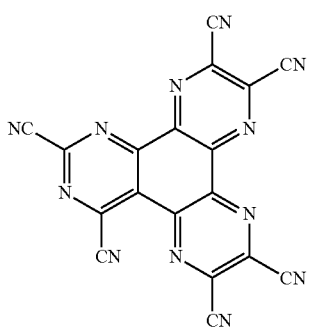
(6)
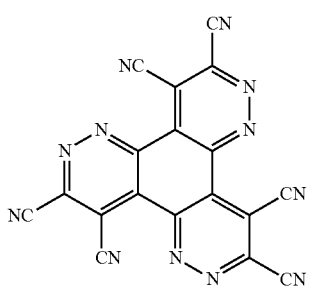
-continued
(7)
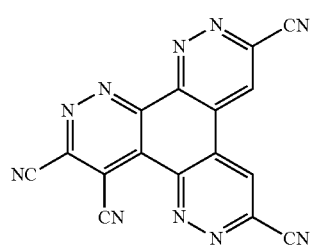
(8)
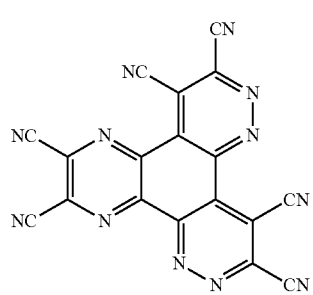
(9)
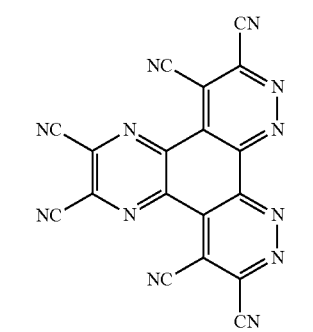
(10)
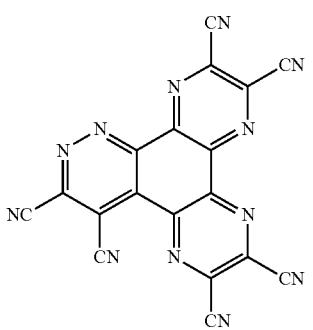
(11)
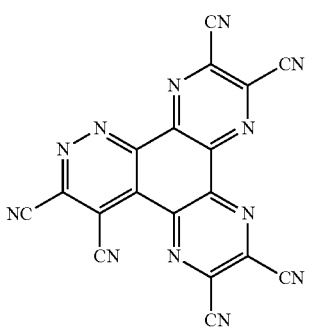

-continued
(12)
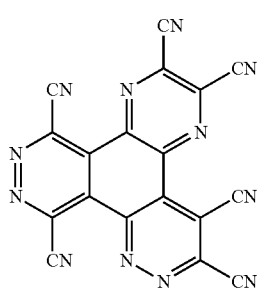
(13)
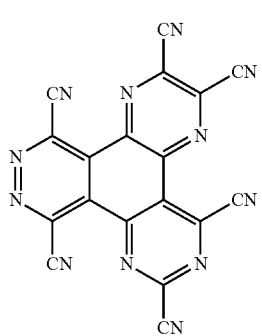
(14)
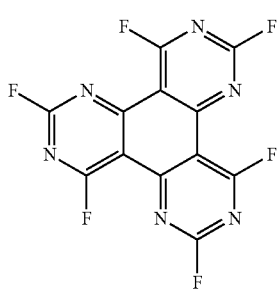
(15)
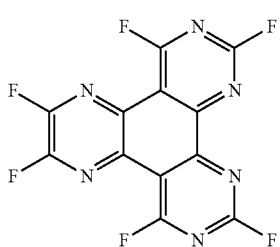
(16)
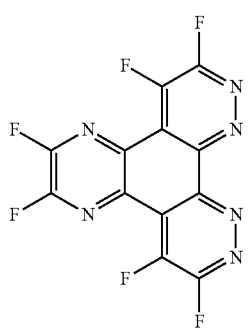
-continued
(17)
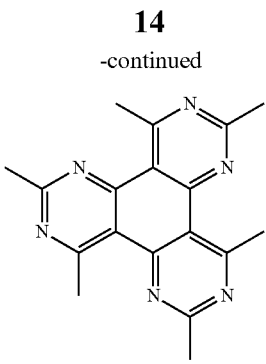
(18)
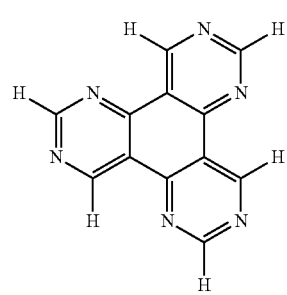
(19)
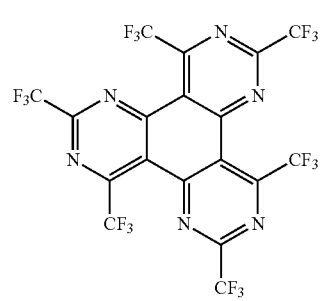
(20)
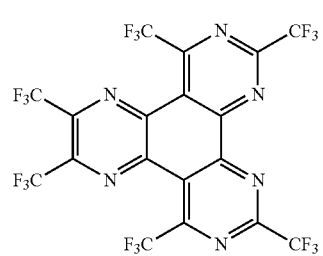
(21)
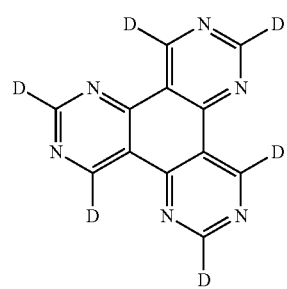

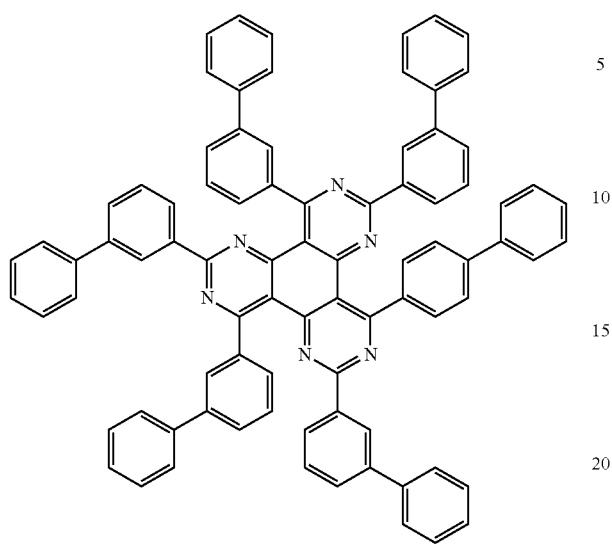
(22)
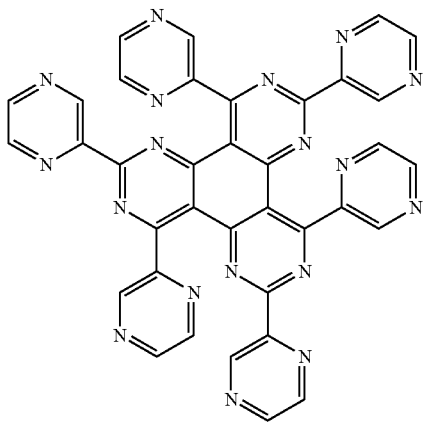
(25)
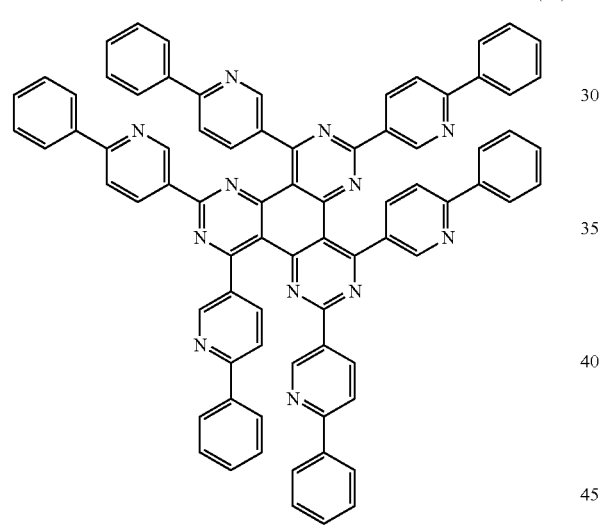
(23)
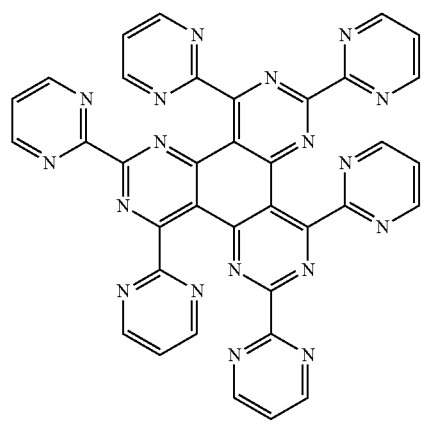
(26)
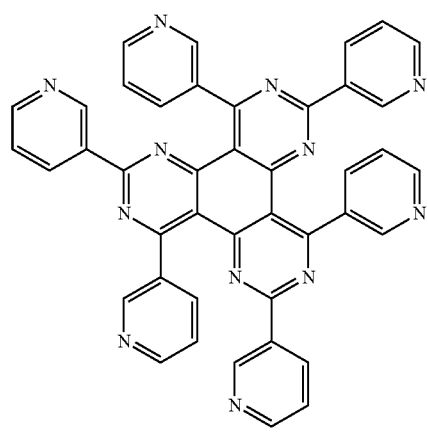
(24)
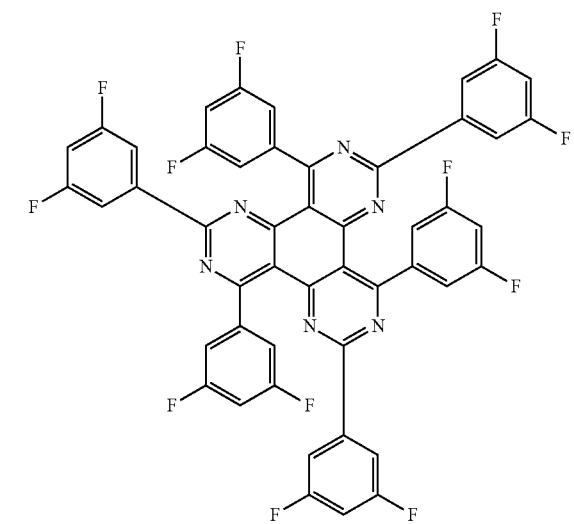
(27)

(28)
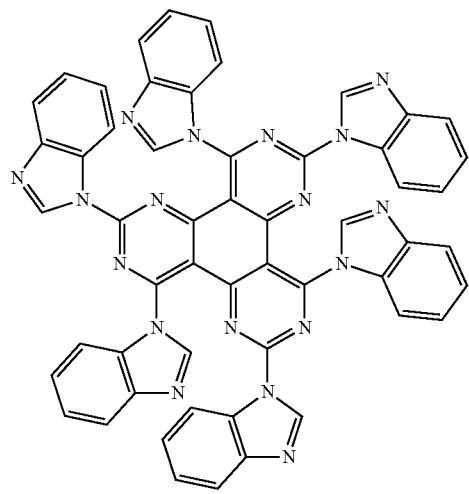
(29)
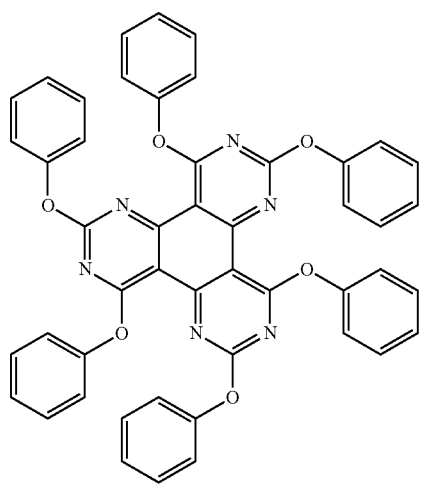
(30)
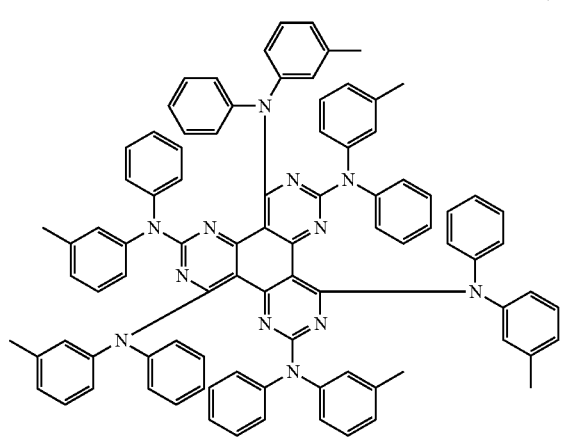
(31)
(32)
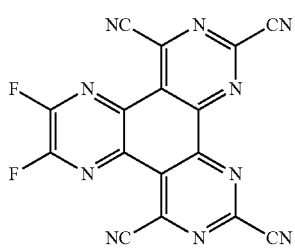
(33)
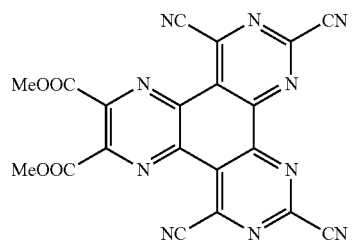
(34)
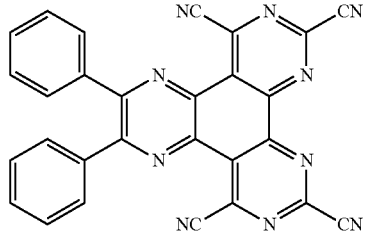
(35)
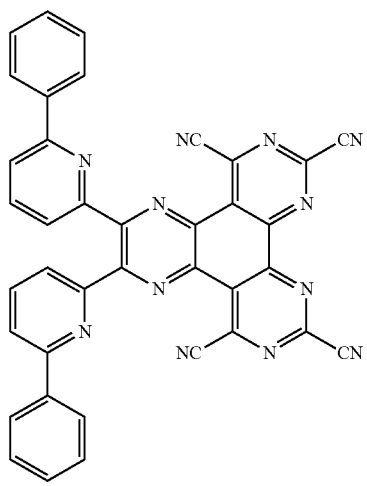

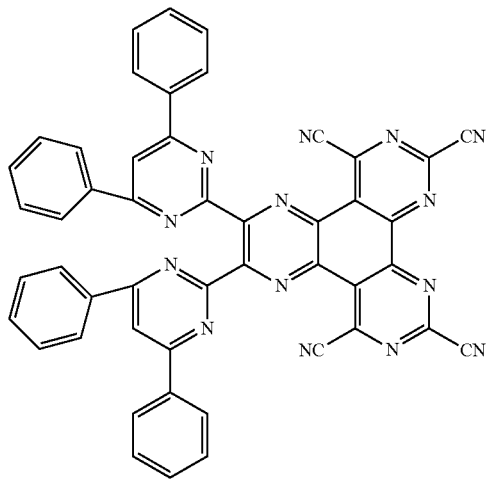
(36)
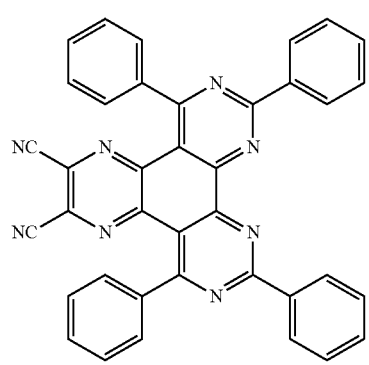
(37)
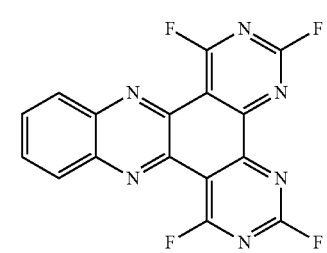
(38)
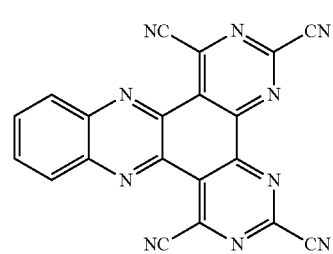
(39)
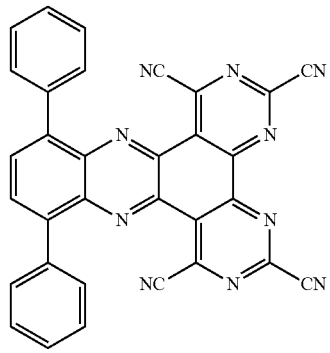
(40)
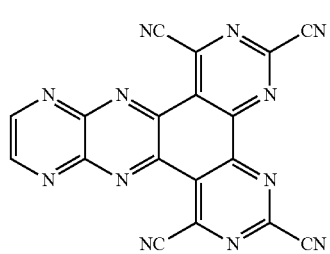
(41)
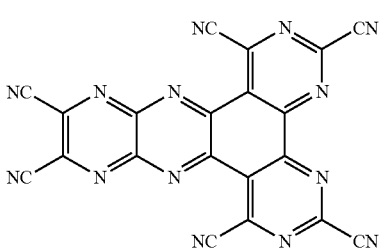
(42)
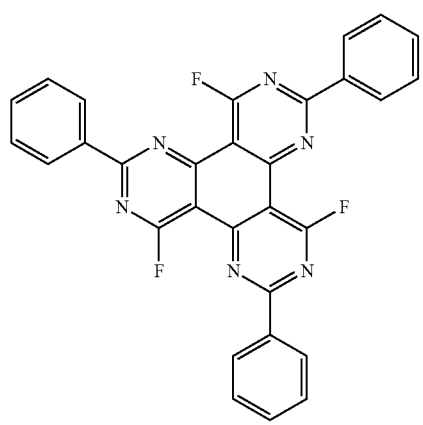
(43)

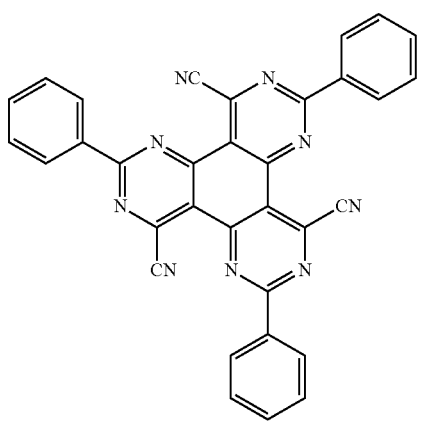
(44)
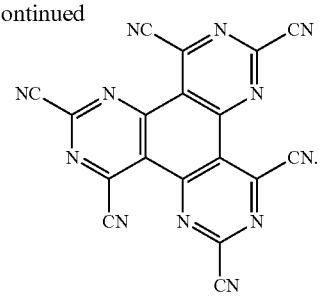
The synthesis of the compounds according to the invention can be carried out by process steps which are generally known to the person skilled in the art of organic synthesis, as depicted by way of example in Scheme 1 for compounds of the formula (2) and in Scheme 2 for compounds of the formula (4).
Scheme 1:
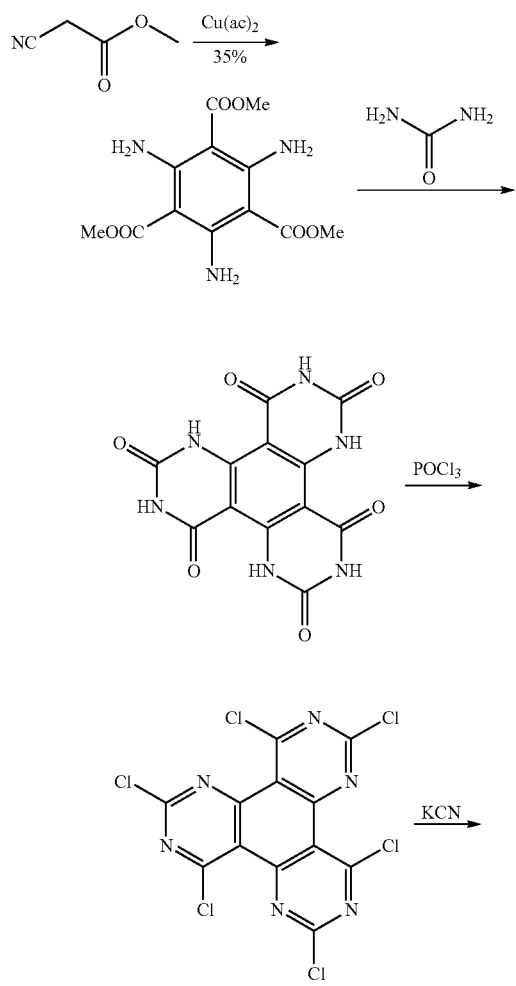
Scheme 2:
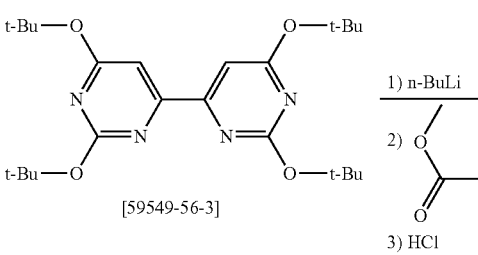
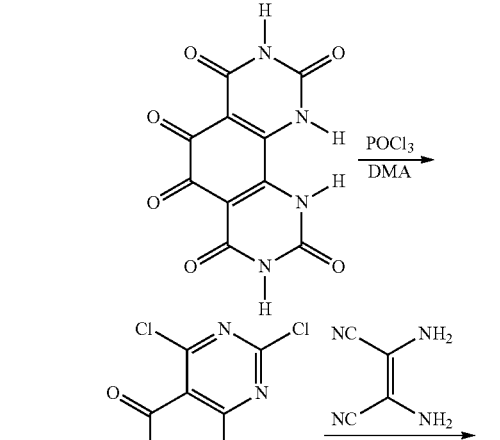
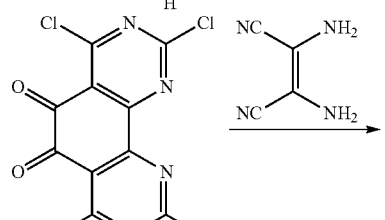
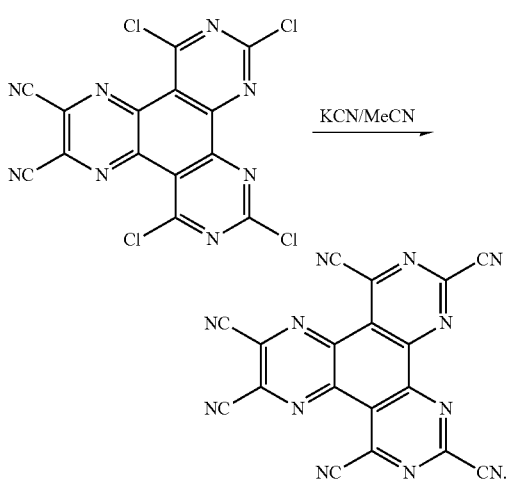

The chlorine substituents may also be replaced by other nucleophiles, for example F, by nucleophilic aromatic substitution, in particular with activation by a Brönsted or Lewis acid. The introduction of other groups, for example substituted amino, alkoxy or thioalkoxy groups, is also possible in this way (Scheme 3).

The introduction of aromatic or heteroaromatic substituents is possible by reaction of the chlorinated compound with organometallic derivatives of aromatic or heteroaromatic compounds, in particular with organolithium compounds or Grignard compounds. Furthermore, palladium-catalysed coupling reactions, in particular with boronic acid Scheme 3:

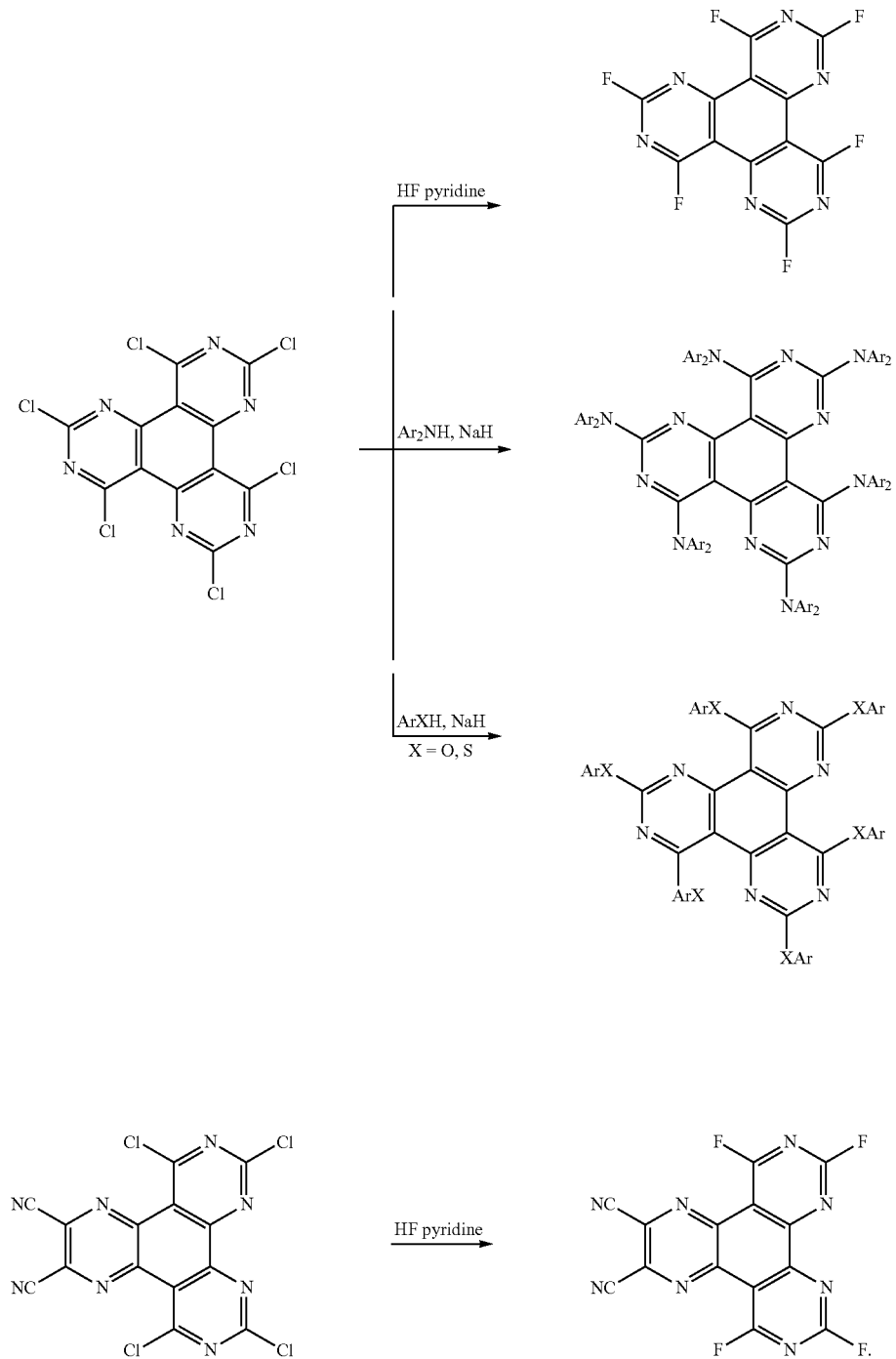

derivatives (Suzuki coupling) or organozinc compounds (Negishi coupling) are possible for the introduction of aromatic substituents (Scheme 4).

Scheme 4:

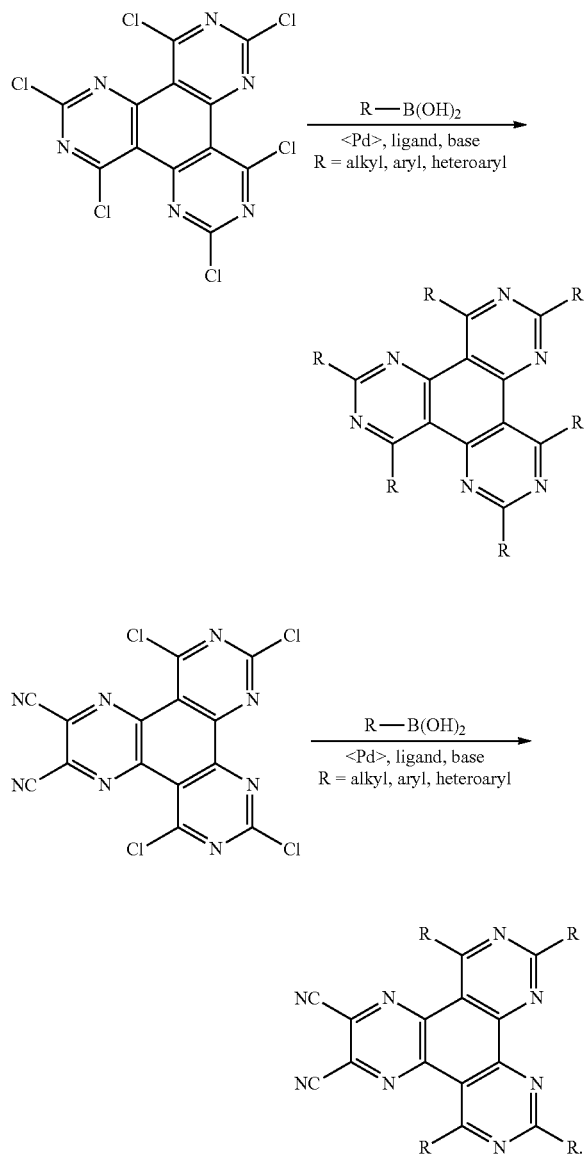

Diarylamino groups can also be introduced by palladium-catalysed Hartwig-Buchwald coupling, alkynes via Sonogashira coupling, alkenes via Heck coupling.

The halogen function can also be converted into an electrophilic group by transmetallation using organolithium compounds or Grignard compounds and are then coupled to a multiplicity of electrophiles, such as, for example, arylboron halides, aldehydes, ketones, nitriles, esters, haloesters, carbon dioxide, arylphosphine halides, halosulfinic acids, haloarylsulfonic acids, etc.

Ortho-quinoid intermediate compounds can be coupled to a multiplicity of vicinal diamines, as shown in Scheme 5 for the example of the intermediate compound 1,3,6,8-tetrachloro-2,4,5,7-tetraazaphenanthrene-9,10-dione.

Scheme 5:

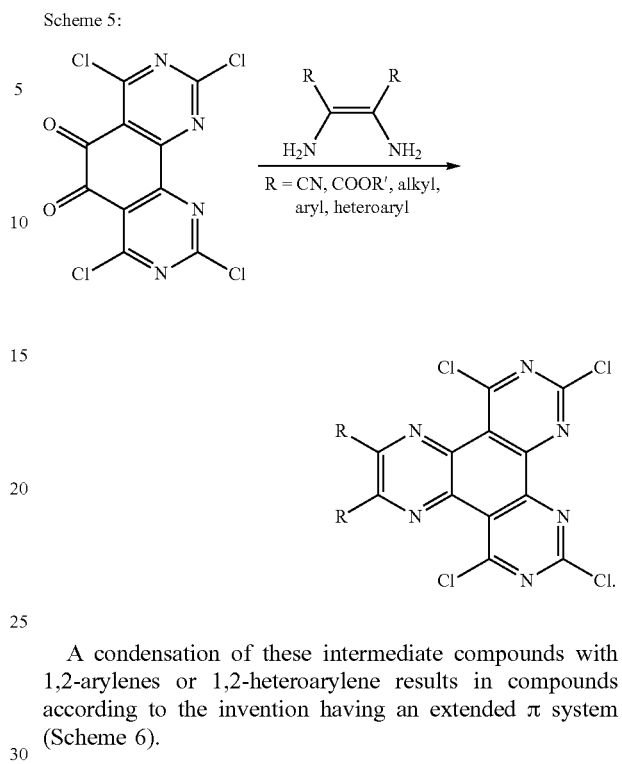

A condensation of these intermediate compounds with 1,2-arylenes or 1,2-heteroarylene results in compounds according to the invention having an extended π system (Scheme 6).

Scheme 6:

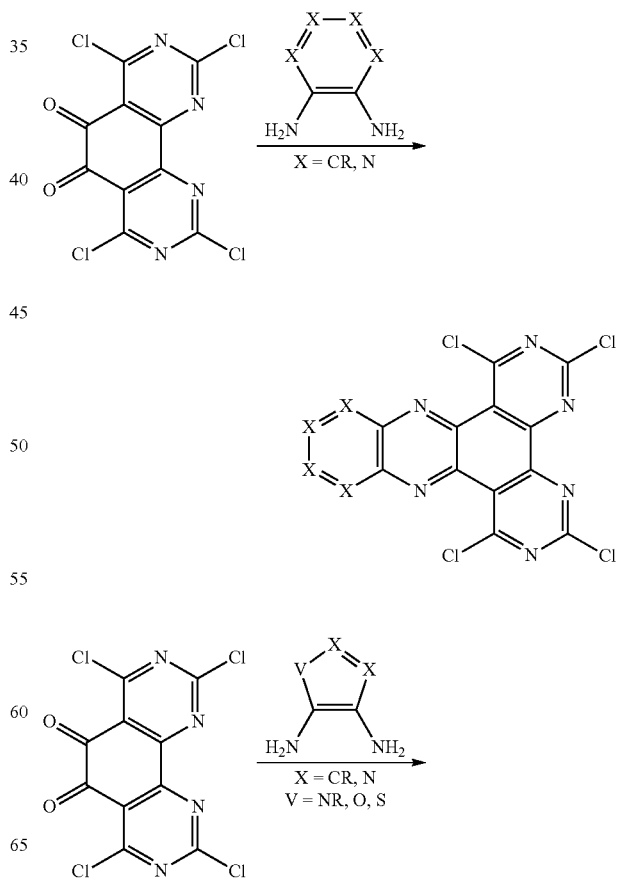

-continued

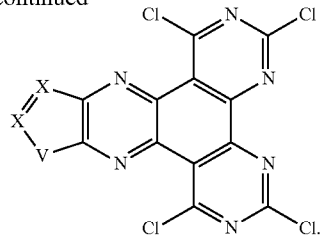

The above-mentioned reactions are generally known to the person skilled in the art of organic chemistry and can be applied by him to the compounds according to the invention without inventive step.

The present invention furthermore relates to a process for the preparation of the compounds according to the invention, characterised by the following reaction steps:
a) synthesis of the corresponding halogenated skeleton; and
b) conversion of the halogen into the desired substituent, in particular by transhalogenation, cyanation, alkoxylation, amination, arylation and/or heteroarylation.

The compounds according to the invention described above, in particular compounds in which at least one group R stands for a reactive leaving group, such as bromine, iodine, triflate, tosylate, boronic acid or boronic acid ester, or a polymerisable group, such as styrene, alkenyl or acrylate, can also be used as monomers for the production of corresponding oligomers, polymers or as core of dendrimers. The oligomerisation or polymerisation here preferably takes place via the halogen functionality or the boronic acid functionality. An oligomer in the sense of this invention is taken to mean a compound which has about 2 to 9 recurring units. A polymer in the sense of this invention has about 10 or more recurring units.

The invention therefore furthermore relates to oligomers, polymers or dendrimers which contain one or more compounds according to the invention, where one or more radicals R represent bonds from the compound to the polymer, oligomer or dendrimer. The polymers, oligomers or dendrimers may be conjugated, partially conjugated or non-conjugated. The oligomers or polymers may be linear or branched. In the structures linked in a linear manner, the units according to the invention may be linked directly to one another or they may be linked to one another via a divalent group, such as, for example, via a substituted or unsubstituted alkylene group, via a heteroatom or via a divalent aromatic or heteroaromatic group. In branched structures, for example, three or more units according to the invention may be linked via a trivalent or polyvalent group, for example via a trivalent or polyvalent aromatic or heteroaromatic group, to give a branched oligomer or polymer.

For the preparation of the oligomers or polymers, the corresponding monomers are homopolymerised or copolymerised with further monomers. Suitable and preferred comonomers are selected from fluorenes (for example in accordance with EP 842208 or WO 00/22026), spirobifluorenes (for example in accordance with EP 707020, EP 894107 or WO 2006/061181), para-phenylenes (for example in accordance with WO 92/18552), carbazoles (for example in accordance with WO 2004/070772 or WO 2004/113468), thiophenes (for example in accordance with EP 1028136), dihydrophenanthrenes (for example in accordance with WO 2005/014689), cis- and trans-indenofluorenes (for example in accordance with WO 2004/041901 or WO 2004/113412), ketones (for example in accordance with WO 2005/040302), phenanthrenes (for example in accordance with WO 2005/104264 or WO 2007/017066) or also a plurality of these units. The polymers, oligomers and dendrimers usually also comprise further units, for example emitting (fluorescent or phosphorescent) units, such as, for example, vinyltriarylamines (for example in accordance with WO 2007/068325) or phosphorescent metal complexes (for example in accordance with WO 2006/003000), and/or charge-transport units. The recurring units according to the invention are particularly suitable as charge-transport units for electrons.

The compounds according to the invention are suitable for use in electronic devices, in particular in organic electroluminescent devices.

The present invention therefore furthermore relates to the use of a compound according to the invention in an electronic device, in particular in an organic electroluminescent device.

The present invention furthermore relates to an electronic device comprising at least one compound according to the invention. The same compounds as mentioned above in the case of product protection are preferred here for the electronic device.

An electronic device in the sense of the present invention is taken to mean a device which comprises anode and cathode and at least one layer arranged between anode and cathode, where this layer comprises at least one organic or organometallic compound. However, it is not necessary for the device to comprise only organic layers. Thus, one or more layers which comprise inorganic materials or consist entirely of inorganic materials may also be present. Likewise, anode and cathode may consist of or comprise purely inorganic materials.

The electronic device is, in particular, selected from the group consisting of organic electroluminescent devices (OLEDs), organic integrated circuits (O-ICs), organic field-effect transistors (O-FETs), organic thin-film transistors (O-TFTs), organic light-emitting transistors (O-LETs), organic solar cells (O-SCs), dye-sensitised solar cells (DSSCs), organic optical detectors, organic photoreceptors, organic field-quench devices (O-FQDs), light-emitting electrochemical cells (LECs), organic laser diodes (O-lasers) and "organic plasmon emitting device" (D. M. Koller et al., *Nature Photonics* 2008, 1-4), but in particular organic electroluminescent devices, organic solar cells and organic field-effect transistors.

The organic electroluminescent device comprises anode, cathode and at least one emitting layer, where at least one organic layer, which may be the emitting layer or another layer, comprises at least one compound according to the invention or a corresponding oligomer, polymer or dendrimer.

Apart from cathode, anode and the emitting layer, the organic electroluminescent device may also comprise further layers. These are selected, for example, from in each case one or more hole-injection layers, hole-transport layers, hole-blocking layers, electron-transport layers, electron-injection layers, electron-blocking layers, exciton-blocking layers, charge-generation layers and/or organic or inorganic p/n junctions. Furthermore, the layers, in particular the charge-transport layers, may also be doped. Doping of the layers may be advantageous for improved charge transport. However, it should be pointed out that each of these layers does not necessarily have to be present, and the choice of layers is always dependant on the compounds used and in particular also on whether the electroluminescent device is fluorescent or phosphorescent.

In an embodiment of the invention, the organic electroluminescent device comprises a plurality of emitting layers, where at least one organic layer, which may be an emitting layer or another layer, comprises at least one compound according to the invention. These emission layers particularly preferably have in total a plurality of emission maxima between 380 nm and 750 nm, resulting overall in white emission, i.e. various emitting compounds which are able to fluoresce or phosphoresce and emit blue and yellow, orange or red light are used in the emitting layers. Particular preference is given to three-layer systems, i.e. systems having three emitting layers, where the three layers exhibit blue, green and orange or red emission (for the basic structure see, for example, WO 2005/011013). Emitters which have broad-band emission bands and thus exhibit white emission are likewise suitable for white emission. It is alos possible to achieve a white-emitting OLED as tandem OLED.

In a preferred embodiment of the invention, the compounds according to the invention are used as hole-injection or hole-transport material. This applies, in particular, if at least one substituent R, preferably at least two substituents R, particularly preferably at least three substituents R, very particularly preferably all substituents R, stand for an electron-deficient group. In contrast to triarylamine derivatives, which are usually used in the hole-injection or hole-transport layer and in which hole transport takes place via the HOMO (highest occupied molecular orbital) of the corresponding compound, hole transport in compounds according to the invention does not take place via the HOMO, but instead via the LUMO (lowest unoccupied molecular orbital). Particularly preferred substituents R are then selected from the group consisting of CN, F, $NO_2$, $CF_3$ and substituted or unsubstituted electron-deficient heterocycles. The electron-deficient heterocycles here are preferably selected from pyridine, pyrazine, pyrimidine, pyridazine, triazine, pyrrole, imidazole, triazole, benzimidazole, quinoline, isoquinoline, quinoxaline, thiadiazole, thiazole, oxadiazole or heteroaromatic ring systems which contain these heteroaryl groups; each of these may be substituted by one or more radicals $R^1$. Since the LUMO of these compounds is as low or even lower compared with the hexaazatriphenylene derivatives used as hole-injection materials in accordance with the prior art, the compounds according to the invention are just as suitable or better as hole-injection or hole-transport materials than the materials in accordance with the prior art. In addition, many of the compounds according to the invention have a higher triplet level compared with the compounds in accordance with the prior art. In the sense of this invention, a hole-injection material is intended to be taken to mean a compound which is employed in a hole-injection layer. A hole-injection layer in the sense of this invention is a layer which is directly adjacent to the anode. In the structure of the organic electroluminescent device, the hole-injection layer is usually followed by a hole-transport layer, so that the hole-injection layer is located between the anode and a hole-transport layer. A hole-transport layer in the sense of the present invention is a layer which is located between a hole-injection layer and the emitting layer.

In a preferred embodiment of the invention, the electroluminescent device according to the invention has a structure comprising, in this sequence: anode-hole-injection layer comprising at least one compound according to the invention-hole-transport layer, preferably comprising at least one triarylamine derivative-emitting layer-cathode. It is likewise possible in this structure to use two or more hole-transport layers, which preferably all comprise at least one triarylamine derivative. A further preferred structure of the electroluminescent device comprises, in this sequence: anode-hole-injection layer, preferably comprising at least one triarylamine derivative-hole-transport layer comprising at least one compound according to the invention-hole-transport layer, preferably comprising at least one triarylamine derivative-emitting layer-cathode. It is likewise possible in this structure for a further hole-transport layer, preferably comprising at least one triarylamine derivative, to be introduced between the hole-injection layer and the layer comprising the compound according to the invention and/or for two or more hole-transport layers, which preferably each comprise at least one triarylamine derivative, to be used instead of a hole-transport layer, which preferably comprises a triarylamine derivative, between the layer comprising the compound according to the invention and the emitting layer. In addition, these devices may furthermore comprise one or more of the further layers mentioned above, for example electron-transport layers, etc. The hole-transport layers here may in each case also be p-doped.

In still a further embodiment of the invention, the compounds according to the invention are employed as electron-transport material or as hole-blocking material in an electron-transport layer or hole-blocking layer. A hole-blocking layer in the sense of this invention is a layer which is located between an emitting layer and an electron-transport layer and is directly adjacent to the emitting layer. It is in each case preferred here for the substituents R to stand, identically or differently on each occurrence, for an aromatic or heteroaromatic ring system, which is preferably selected from the groups mentioned above. It may furthermore be preferred for the compound to be doped with electron-donor compounds. This applies, in particular, to use in an electron-transport layer. Suitable dopants are alkali metals or alkali metal complexes or compounds, in particular lithium compounds, for example lithium quinolinate.

In still a further embodiment of the invention, the compounds according to the invention are employed as charge-generation material in a charge-generation layer. This is used, for example, in a tandem OLED.

In still a further embodiment of the invention, the compounds according to the invention are employed as matrix material for an emitting compound, in particular for a phosphorescent compound. This applies, in particular, to compounds in which R stands for an aryl or heteroaryl group. The phosphorescent compound here is preferably a red- or green-phosphorescent compound.

In the above-mentioned functions, i.e., in particular, as hole-injection or -transport material, as electron-transport material or as charge-generation material, the materials are also suitable for other organic electronic devices, as have been mentioned above.

The cathode of the electronic device according to the invention is preferably metals having a low work function, metal alloys or multilayered structures comprising various metals, such as, for example, alkaline-earth metals, alkali metals, main-group metals or lanthanoids (for example Ca, Ba, Mg, Al, In, Mg, Yb, Sm, etc.). In the case of multilayered structures, further metals which have a relatively high work function, such as, for example, Ag, can also be used in addition to the said metals, in which case combinations of the metals, such as, for example, Mg/Ag, Ca/Ag or Ba/Ag, are then generally used. Preference is likewise given to metal alloys, in particular alloys comprising an alkali metal or alkaline-earth metal and silver, particularly preferably an alloy of Mg and Ag. It may also be preferred to introduce a thin interlayer of a material having a high dielectric constant between a metallic cathode and the organic semiconductor. Suitable for this purpose are, for example, alkali metal or alkaline-earth metal fluorides, or the corresponding oxides or carbonates (for example LiF, $Li_2O$, CsF, $Cs_2CO_3$, $BaF_2$, MgO, NaF, etc.), but also other alkali metal and alkaline-earth metal compounds, such as, for example, lithium quinolinate. The layer thickness of this interlayer is preferably between 0.5 and 5 nm.

The anode of the electronic device according to the invention is preferably materials having a high work function. The anode preferably has a work function of greater than 4.5 eV vs. vacuum. Suitable for this purpose are on the one hand metals having a high redox potential, such as, for example, Ag, Pt or Au. On the other hand, metal/metal oxide electrodes (for example Al/Ni/$NiO_x$, Al/$PtO_x$) may also be preferred. For some applications, at least one of the electrodes must be transparent or partially transparent in order either to facilitate irradiation of the organic material (O-SCs) or the coupling-out of light (OLEDs/PLEDs, O-lasers). Preferred anode materials for transparent or partially transparent anodes are conductive mixed metal oxides. Particular preference is given to indium-tin oxide (ITO) or indiumzinc oxide (IZO). Preference is furthermore given to conductive, doped organic materials, in particular conductive, doped polymers.

The device is correspondingly (depending on the application) structured, provided with contacts and finally hermetically sealed, since the lifetime of such devices is drastically shortened in the presence of water and/or air.

In general, all further materials as employed in accordance with the prior art in organic electroluminescent devices can also be employed in combination with the compounds according to the invention. The emitting layer here may comprise fluorescent and/or phosphorescent dopants, preferably in each case in combination with a matrix material (host material).

Suitable fluorescent dopants are selected from the class of the monostyrylamines, the distyrylamines, the tristyrylamines, the tetrastyrylamines, the styrylphosphines, the styryl ethers and the arylamines. A monostyrylamine is taken to mean a compound which contains one substituted or unsubstituted styryl group and at least one, preferably aromatic, amine. A distyrylamine is taken to mean a compound which contains two substituted or unsubstituted styryl groups and at least one, preferably aromatic, amine. A tristyrylamine is taken to mean a compound which contains three substituted or unsubstituted styryl groups and at least one, preferably aromatic, amine. A tetrastyrylamine is taken to mean a compound which contains four substituted or unsubstituted styryl groups and at least one, preferably aromatic, amine. The styryl groups are particularly preferably stilbenes, which may also be further substituted. Corresponding phosphines and ethers are defined analogously to the amines. An arylamine or aromatic amine in the sense of this invention is taken to mean a compound which contains three substituted or unsubstituted aromatic or heteroaromatic ring systems bonded directly to the nitrogen. At least one of these aromatic or heteroaromatic ring systems is preferably a condensed ring system, particularly preferably having at least 14 aromatic ring atoms. Preferred examples thereof are aromatic anthracenamines, aromatic anthracenediamines, aromatic pyrenamines, aromatic pyrenediamines, aromatic chrysenamines or aromatic chrysenediamines. An aromatic anthracenamine is taken to mean a compound in which one diarylamino group is bonded directly to an anthracene group, preferably in the 9-position. An aromatic anthracenediamine is taken to mean a compound in which two diarylamino groups are bonded directly to an anthracene group, preferably in the 9,10-position. Aromatic pyrenamines, pyrenediamines, chrysenamines and chrysenediamines are defined analogously thereto, where the diarylamino groups are preferably bonded to the pyrene in the 1-position or in the 1,6-position. Further preferred dopants are selected from indenofluorenamines or indenofluorenediamines, for example in accordance with WO 2006/122630, benzoindenofluorenamines or benzoindenofluorenediamines, for example in accordance with WO 2008/006449, and dibenzoindenofluorenamines or dibenzoindenofluorenediamines, for example in accordance with WO 2007/140847. Examples of dopants from the class of the styrylamines are substituted or unsubstituted tristilbenamines or the dopants described in WO 2006/000388, WO 2006/058737, WO 2006/000389, WO 2007/065549 and WO 2007/115610. Preference is furthermore given to the condensed hydrocarbons disclosed in WO 2010/012328.

Suitable host materials for the fluorescent emitters are selected from the classes of the oligoarylenes (for example 2,2',7,7'-tetraphenylspirobifluorene in accordance with EP 676461 or dinaphthylanthracene), in particular the oligoarylenes containing condensed aromatic groups, the oligoarylenevinylenes (for example DPVBi or spiro-DPVBi in accordance with EP 676461), the polypodal metal complexes (for example in accordance with WO 2004/081017), the hole-conducting compounds (for example in accordance with WO 2004/058911), the electron-conducting compounds, in particular ketones, phosphine oxides, sulfoxides, etc. (for example in accordance with WO 2005/084081 and WO 2005/084082), the atropisomers (for example in accordance with WO 2006/048268), the boronic acid derivatives (for example in accordance with WO 2006/117052), the benzanthracenes (for example in accordance with WO 2008/145239) or the benzophenanthrenes (for example in accordance with WO 2010/083869). Particularly preferred host materials are selected from the classes of the oligoarylenes, comprising naphthalene, anthracene, benzanthracene, benzophenanthrene and/or pyrene, or atropisomers of these compounds, the oligoarylenevinylenes, the ketones, the phosphine oxides and the sulfoxides. Very particularly preferred host materials are selected from the classes of the oligoarylenes, comprising anthracene, benzanthracene, benzophenanthrene and/or pyrene, or atropisomers of these compounds. An oligoarylene in the sense of this invention is intended to be taken to mean a compound in which at least three aryl or arylene groups are bonded to one another. Suitable host materials are furthermore, for example, materials as disclosed in WO 2004/018587, WO 2008/006449, U.S. Pat. No. 5,935,721, US 2005/0181232, JP 2000/273056, EP 681019, US 2004/0247937 and US 2005/0211958.

Suitable phosphorescent compounds are, in particular, compounds which emit light, preferably in the visible region, on suitable excitation and in addition contain at least one atom having an atomic number of greater than 20, preferably greater than 38 and less than 84, particularly preferably greater than 56 and less than 80. The phosphorescent emitters used are preferably compounds which contain copper, molybdenum, tungsten, rhenium, ruthenium, osmium, rhodium, iridium, palladium, platinum, silver, gold or europium, in particular compounds which contain iridium or platinum. In the sense of the present application, all luminescent metal complexes which contain the above-mentioned metal are referred to as phosphorescent compounds.

Examples of suitable phosphorescent emitters are revealed by the applications WO 00/70655, WO 2001/41512, WO 2002/02714, WO 2002/15645, EP 1191613, EP 1191612, EP 1191614, WO 2004/081017, WO 2005/

033244, WO 2005/042550, WO 2005/113563, WO 2006/008069, WO 2006/061182, WO 2006/081973, WO 2009/146770, WO 2010/086089 and the unpublished application EP 10006208.2 and DE 102010027317.1. In general, all phosphorescent complexes as used in accordance with the prior art for phosphorescent OLEDs and as are known to the person skilled in the art in the area of organic electroluminescence are suitable, and the person skilled in the art will be able to use further phosphorescent compounds without inventive step.

Suitable matrix materials for the phosphorescent emitters are selected from the group consisting of aromatic ketones, phosphine oxides, sulfoxides and sulfones, for example in accordance with WO 2004/013080, WO 2004/093207, WO 2006/005627 or WO 2010/006680, triarylamines, carbazole derivatives, for example CBP (N,N-biscarbazolylbiphenyl) or the carbazole derivatives disclosed in WO 2005/039246, US 2005/0069729, JP 2004/288381, EP 1205527 or WO 2008/086851, cis- and trans-indolocarbazole derivatives, for example in accordance with WO 2007/063754 or WO 2008/056746, cis- and trans-indenocarbazole derivatives, for example in accordance with WO 2010/136109, azacarbazoles, for example in accordance with EP 1617710, EP 1617711, EP 1731584, JP 2005/347160, bipolar matrix materials, for example in accordance with WO 2007/137725, silanes, for example in accordance with WO 2005/111172, azaboroles or boronic esters, for example in accordance with WO 2006/117052, triazine derivatives, for example in accordance with WO 2010/015306, WO 2007/063754 or WO 2008/056746, and zinc complexes, for example in accordance with WO 2009/062578.

Suitable charge-transport materials, as can be used in the hole-injection or hole-transport layer or in the electron-transport layer of the organic electroluminescent device according to the invention, are, apart from the materials according to the invention, for example, the compounds disclosed in Y. Shirota et al., *Chem. Rev.* 2007, 107(4), 953-1010, or other materials, as employed in accordance with the prior art in these layers.

Examples of preferred hole-transport materials which can be used in a hole-transport or hole-injection layer in the electroluminescent device according to the invention are indenofluorenamines and derivatives (for example in accordance with WO 2006/122630, WO 2006/100896 or DE 102008024182), the amine derivatives disclosed in EP 1661888, hexaazatriphenylene derivatives (for example in accordance with WO 2001/049806), amine derivatives containing condensed aromatic rings (for example in accordance with U.S. Pat. No. 5,061,569), the amine derivatives disclosed in WO 95/09147, monobenzoindenofluorenamines (for example in accordance with WO 2008/006449) or dibenzoindenofluorenamines (for example in accordance with WO 2007/140847). Hole-transport and hole-injection materials which are furthermore suitable are derivatives of the above-mentioned compounds, as disclosed in JP 2001/226331, EP 676461, EP 650955, WO 01/049806, U.S. Pat. No. 4,780,536, WO 98/30071, EP 891121, EP 1661888, JP 2006/253445, EP 650955, WO 2006/073054 and U.S. Pat. No. 5,061,569.

Suitable hole-transport or hole-injection materials are furthermore, for example, the materials indicated in the following table.

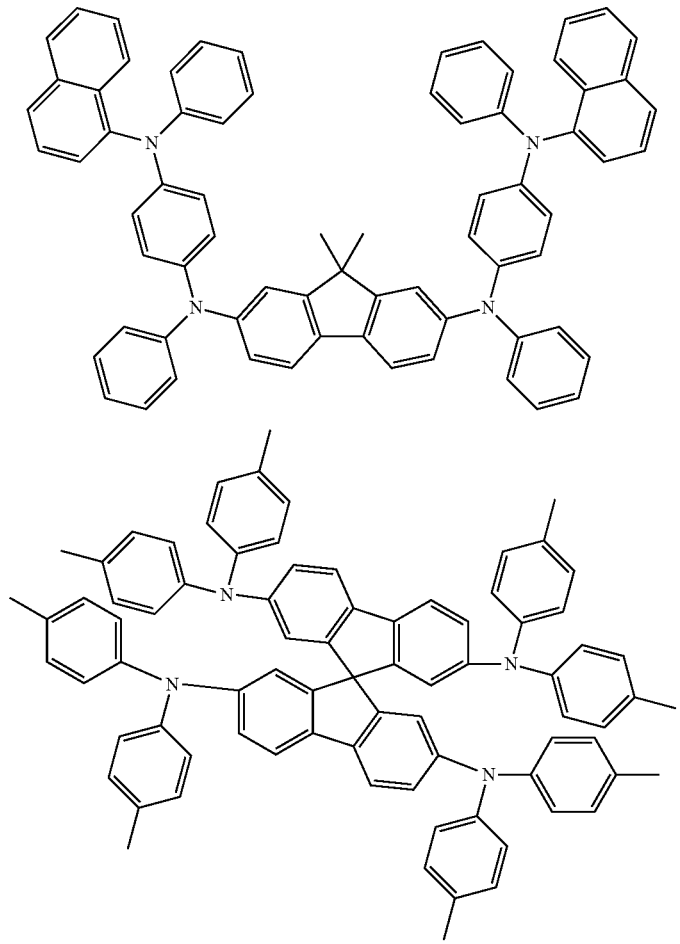

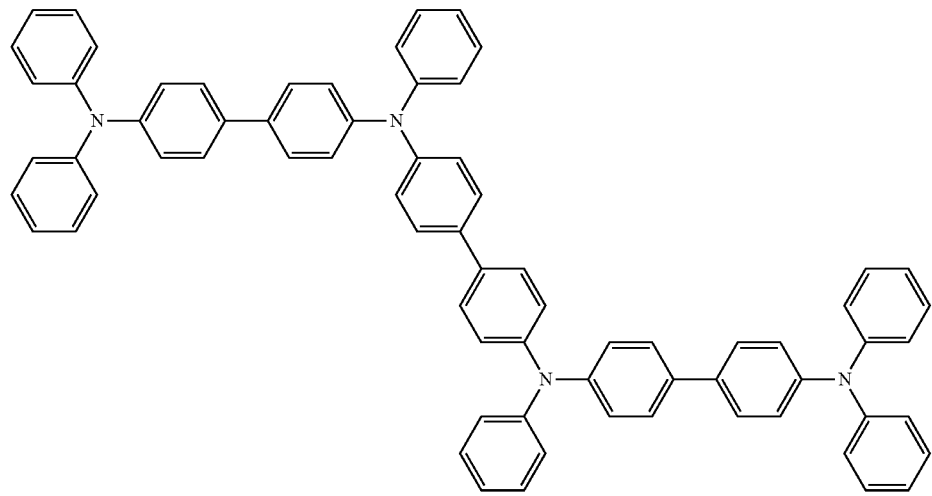 [SMILES: c1ccc(N(c2ccccc2)c2ccc(-c3ccc(N(c4ccccc4)c4ccc(-c5ccc(N(c6ccccc6)c6ccc(-c7ccc(N(c8ccccc8)c8ccccc8)cc7)cc6)cc5)cc4)cc3)cc2)cc1]
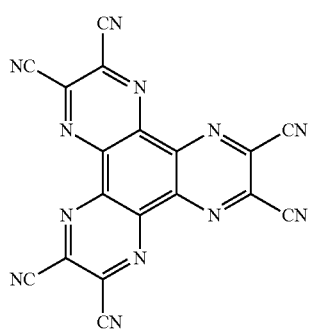 [SMILES: N#Cc1nc2c3nc(C#N)c(C#N)nc3c3nc(C#N)c(C#N)nc3c2nc1C#N]
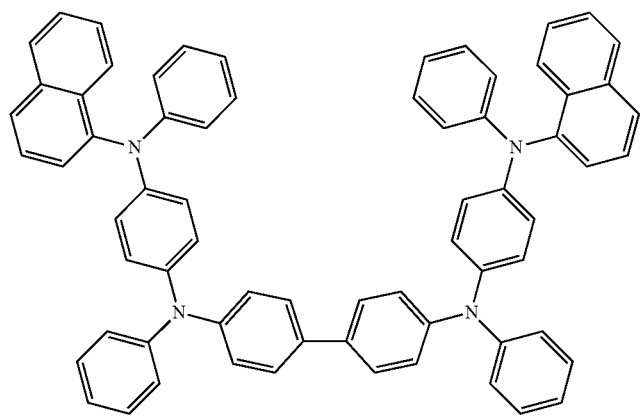 [SMILES: c1ccc(N(c2ccc(-c3ccc(N(c4ccccc4)c4ccc(N(c5ccccc5)c5cccc6ccccc56)cc4)cc3)cc2)c2ccc(N(c3ccccc3)c3cccc4ccccc34)cc2)cc1]

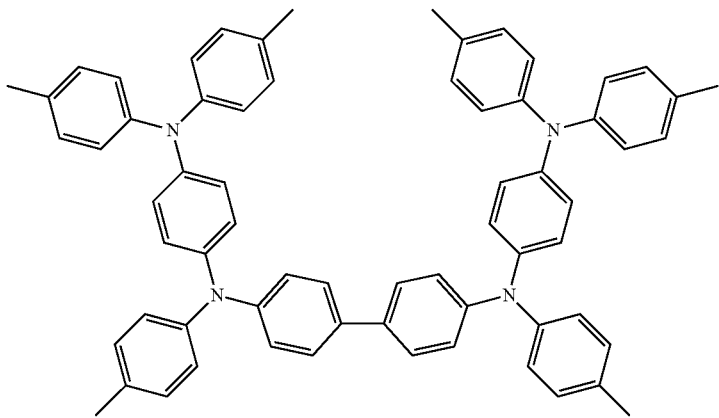
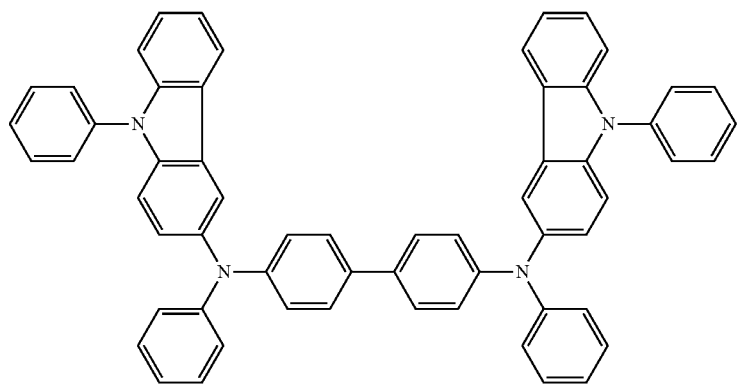 [SMILES: c1ccc(N(c2ccc(-c3ccc(N(c4ccccc4)c4ccc5c(c4)c4ccccc4n5-c4ccccc4)cc3)cc2)c2ccc3c(c2)c2ccccc2n3-c2ccccc2)cc1]
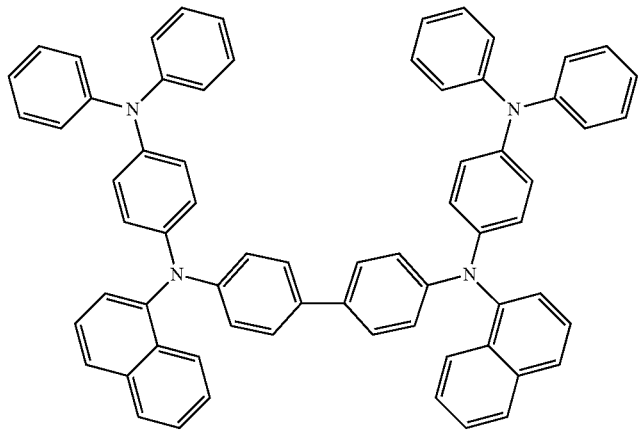 [SMILES: c1ccc(N(c2ccccc2)c2ccc(N(c3ccc(-c4ccc(N(c5ccc(N(c6ccccc6)c6ccccc6)cc5)c5cccc6ccccc56)cc4)cc3)c3cccc4ccccc34)cc2)cc1]

-continued
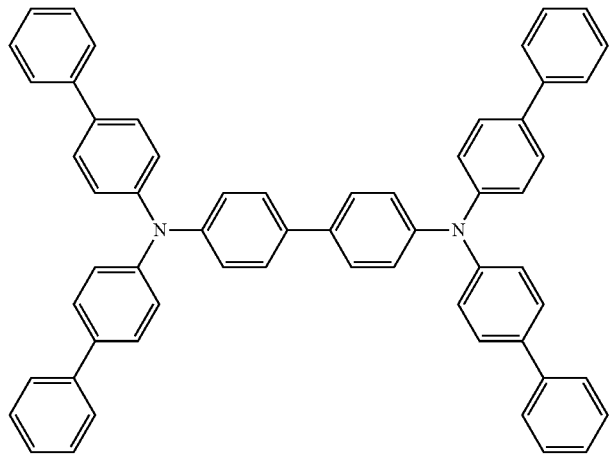 [SMILES: c1ccc(-c2ccc(N(c3ccc(-c4ccccc4)cc3)c3ccc(-c4ccc(N(c5ccc(-c6ccccc6)cc5)c5ccc(-c6ccccc6)cc5)cc4)cc3)cc2)cc1]
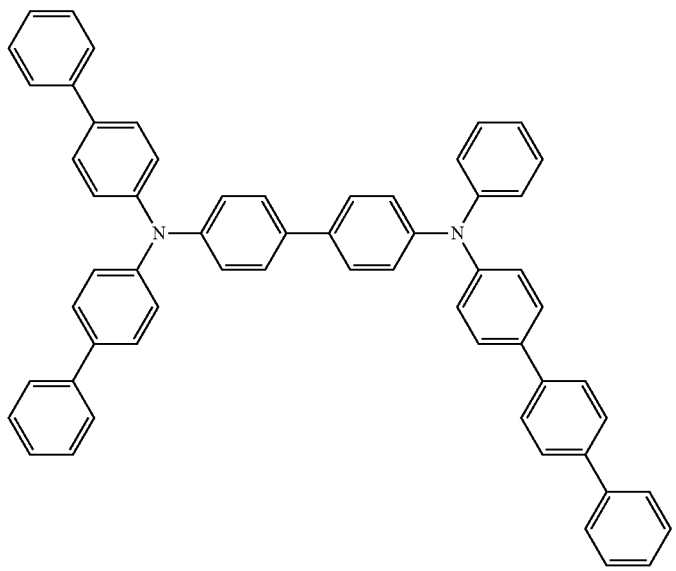 [SMILES: c1ccc(-c2ccc(-c3ccc(N(c4ccccc4)c4ccc(-c5ccc(N(c6ccc(-c7ccccc7)cc6)c6ccc(-c7ccccc7)cc6)cc5)cc4)cc3)cc2)cc1]
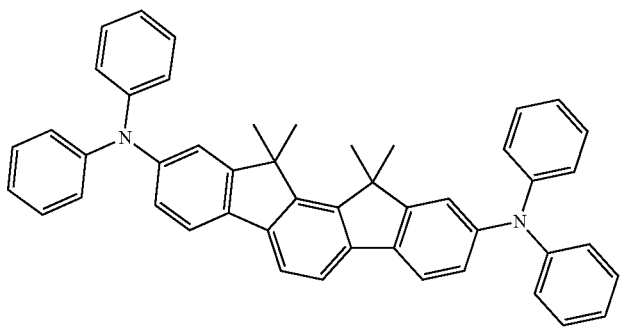 [SMILES: CC1(C)c2cc(N(c3ccccc3)c3ccccc3)ccc2-c2ccc3c(c21)C(C)(C)c1cc(N(c2ccccc2)c2ccccc2)ccc1-3]
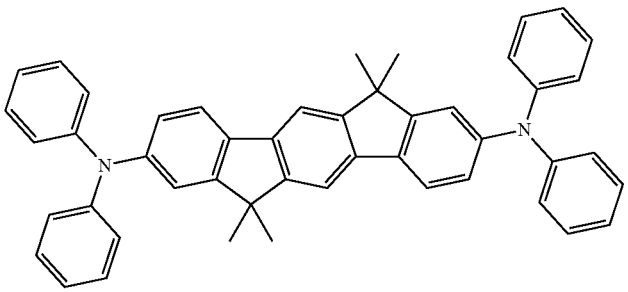 [SMILES: CC1(C)c2cc(N(c3ccccc3)c3ccccc3)ccc2-c2cc3c(cc21)-c1ccc(N(c2ccccc2)c2ccccc2)cc1C3(C)C]

-continued
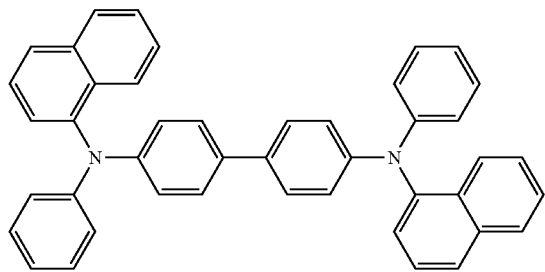 [SMILES: c1ccc(N(c2ccc(-c3ccc(N(c4ccccc4)c4cccc5ccccc45)cc3)cc2)c2cccc3ccccc23)cc1]
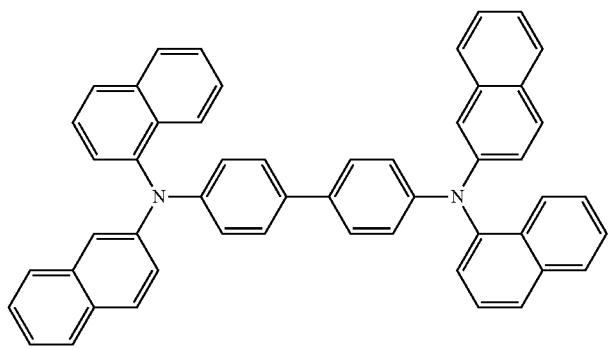 [SMILES: c1ccc2cc(N(c3ccc(-c4ccc(N(c5ccc6ccccc6c5)c5cccc6ccccc56)cc4)cc3)c3cccc4ccccc34)ccc2c1]
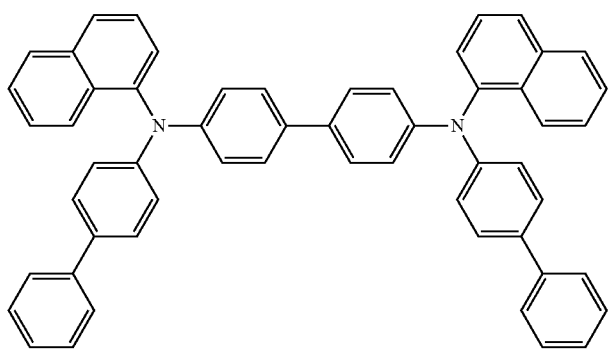 [SMILES: c1ccc(-c2ccc(N(c3ccc(-c4ccc(N(c5ccc(-c6ccccc6)cc5)c5cccc6ccccc56)cc4)cc3)c3cccc4ccccc34)cc2)cc1]
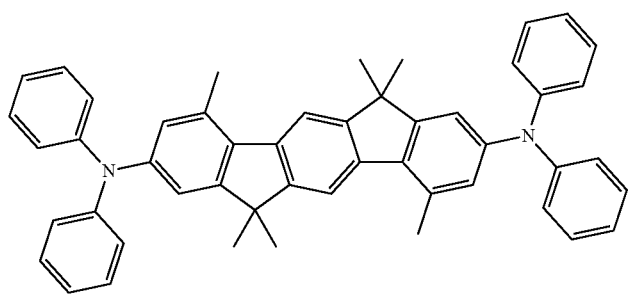 [SMILES: Cc1cc(N(c2ccccc2)c2ccccc2)cc2c1-c1cc3c(cc1C2(C)C)-c1c(C)cc(N(c2ccccc2)c2ccccc2)cc1C3(C)C]

-continued
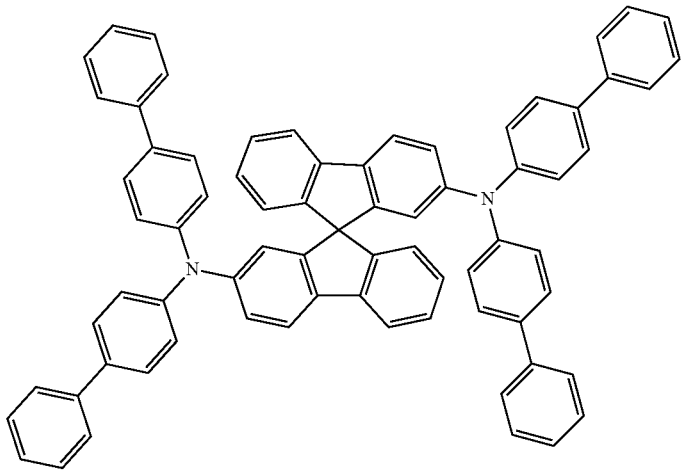 [SMILES: c1ccc(-c2ccc(N(c3ccc(-c4ccccc4)cc3)c3ccc4c(c3)C3(c5ccccc5-4)c4ccccc4-c4ccc(N(c5ccc(-c6ccccc6)cc5)c5ccc(-c6ccccc6)cc5)cc43)cc2)cc1]
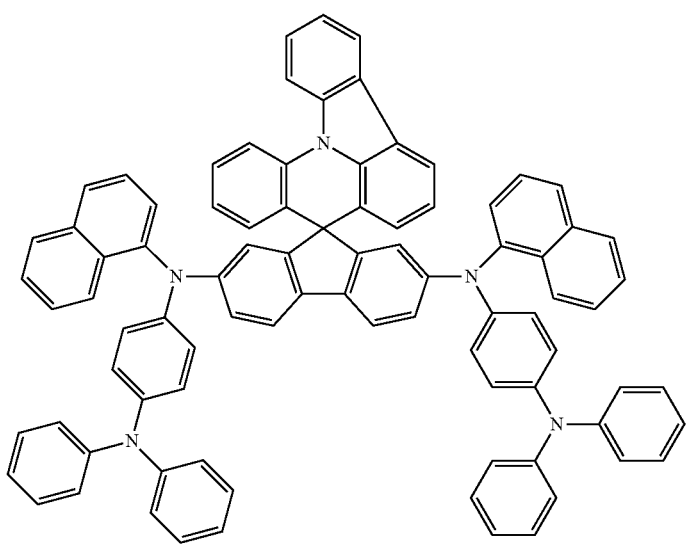 [SMILES: c1ccc(N(c2ccccc2)c2ccc(N(c3ccc4c(c3)C3(c5cc(N(c6ccc(N(c7ccccc7)c7ccccc7)cc6)c6cccc7ccccc67)ccc5-4)c4ccccc4-n4c5ccccc5c5cccc3c54)c3cccc4ccccc34)cc2)cc1]
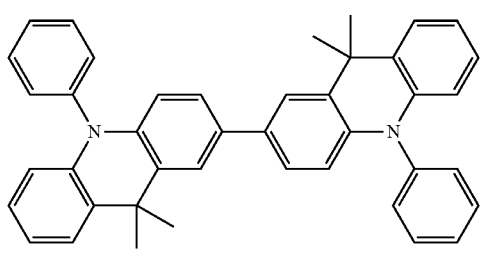 [SMILES: CC1(C)c2ccccc2N(c2ccccc2)c2ccc(-c3ccc4c(c3)C(C)(C)c3ccccc3N4c3ccccc3)cc21]
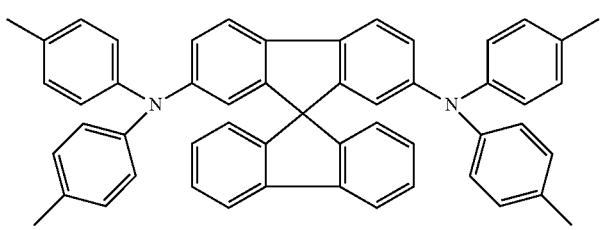

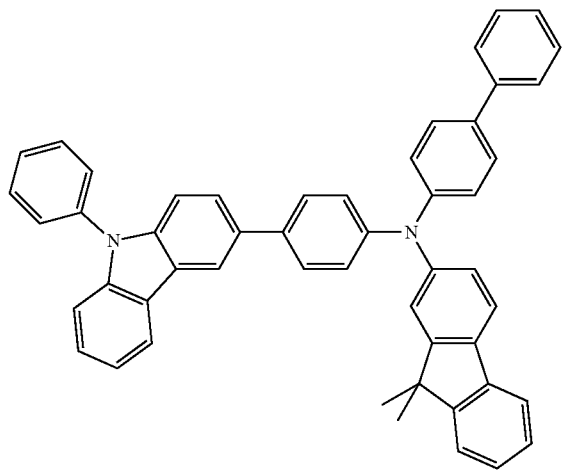 [SMILES: CC1(C)c2ccccc2-c2ccc(N(c3ccc(-c4ccccc4)cc3)c3ccc(-c4ccc5c(c4)c4ccccc4n5-c4ccccc4)cc3)cc21]
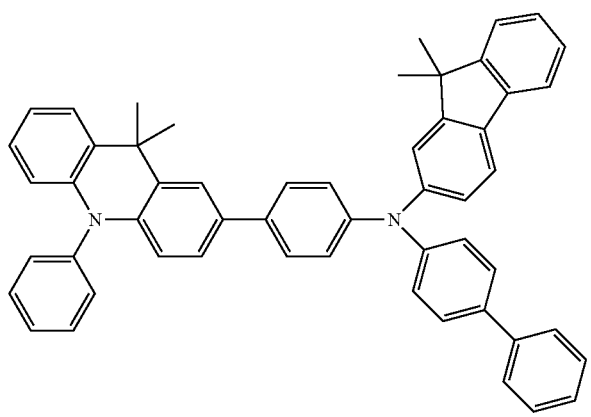 [SMILES: CC1(C)c2ccccc2-c2ccc(N(c3ccc(-c4ccccc4)cc3)c3ccc(-c4ccc5c(c4)C(C)(C)c4ccccc4N5c4ccccc4)cc3)cc21]
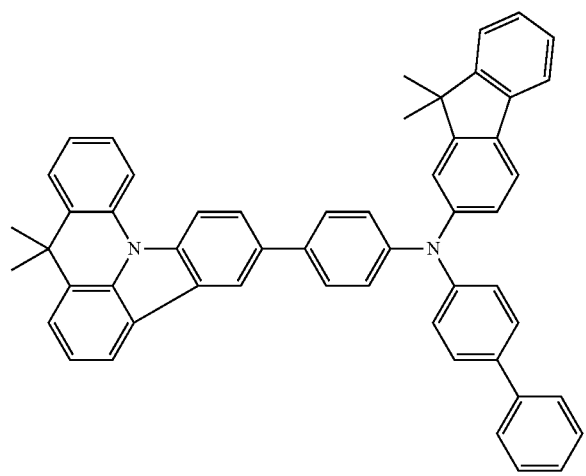 [SMILES: CC1(C)c2ccccc2-c2ccc(N(c3ccc(-c4ccccc4)cc3)c3ccc(-c4ccc5c(c4)c4cccc6c4n5-c4ccccc4C6(C)C)cc3)cc21]

-continued
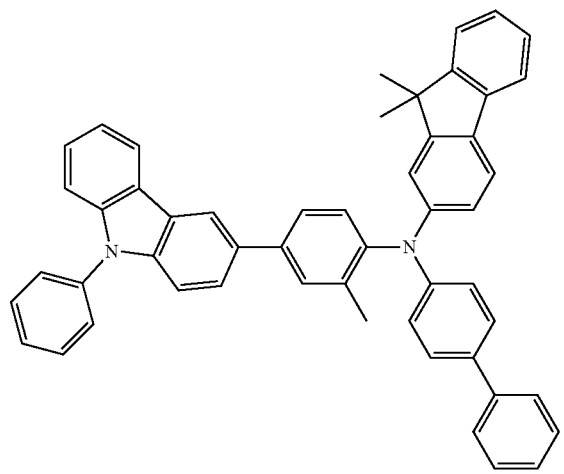 [SMILES: Cc1cc(-c2ccc3c(c2)c2ccccc2n3-c2ccccc2)ccc1N(c1ccc(-c2ccccc2)cc1)c1ccc2c(c1)C(C)(C)c1ccccc1-2]
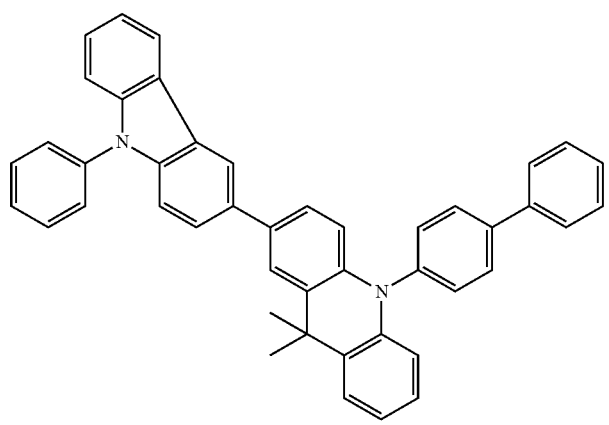 [SMILES: CC1(C)c2ccccc2N(c2ccc(-c3ccccc3)cc2)c2ccc(-c3ccc4c(c3)c3ccccc3n4-c3ccccc3)cc21]
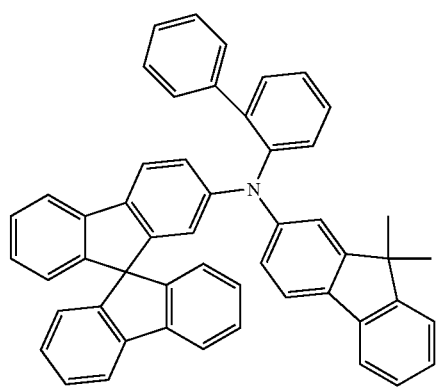 [SMILES: CC1(C)c2ccccc2-c2ccc(N(c3ccc4c(c3)C3(c5ccccc5-c5ccccc53)c3ccccc3-4)c3ccccc3-c3ccccc3)cc21]

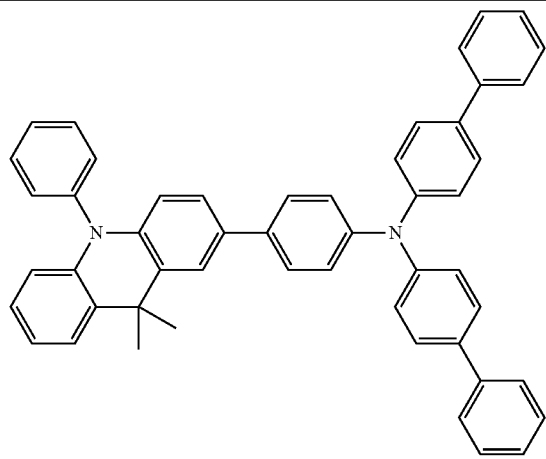

Preference is furthermore given to an organic electroluminescent device, characterised in that one or more layers are coated by means of a sublimation process, in which the materials are vapour-deposited in vacuum sublimation units at an initial pressure of less than $10^{-5}$ mbar, preferably less than $10^{-6}$ mbar. However, it should be noted that the initial pressure may also be even lower, for example less than $10^{-7}$ mbar.

Preference is likewise given to an organic electroluminescent device, characterised in that one or more layers are coated by means of the OVPD (organic vapour phase deposition) process or with the aid of carrier-gas sublimation, in which the materials are applied at a pressure between $10^{-5}$ mbar and 1 bar. A special case of this process is the OVJP (organic vapour jet printing) process, in which the materials are applied directly through a nozzle and are thus structured (for example M. S. Arnold et al., *Appl. Phys. Lett.* 2008, 92, 053301).

Preference is furthermore given to an organic electroluminescent device, characterised in that one or more layers are produced from solution, such as, for example, by spin coating, or by means of any desired printing process, such as, for example, screen printing, flexographic printing or offset printing, but particularly preferably LITI (light induced thermal imaging, thermal transfer printing) or ink-jet printing. Soluble compounds are necessary for this purpose. High solubility can be achieved through suitable substitution of the compounds. It is not only solutions of individual materials that can be applied here, but also solutions which comprise a plurality of compounds, for example matrix material and dopant.

It is also possible to combine a plurality of these processes and, for example, to apply one or more layers by vapour deposition and to apply one or more further layers from solution.

The present invention furthermore relates to the processes mentioned above.

The compounds according to the invention have the following surprising advantages over the prior art on use in organic electroluminescent devices:

1. The compounds according to the invention have high thermal stability and can be sublimed without decomposition.
2. The compounds according to the invention which are substituted by electron-deficient substituents, in particular F, CN and/or electron-deficient heterocycles, are very highly suitable as hole-injection material or as hole-transport material for use in a hole-injection layer or in a hole-transport layer and result in high efficiencies, in particular in high power efficiencies, and long lifetimes in this use.
3. The compounds according to the invention, in particular those which are substituted by aromatic or heteroaromatic groups, are very highly suitable as electron-transport material or as hole-blocking material for use in an electron-transport layer or in a hole-blocking layer and result in high efficiencies, in particular in high power efficiencies, and long lifetimes in this use.
4. The compounds according to the invention have a higher triplet level than hexaazatriphenylene derivatives in accordance with the prior art. They are thus more suitable than the materials in accordance with the prior art for use in combination with triplet emitters, in particular if the compounds according to the invention are used as triplet matrix material or are employed in a layer which is directly adjacent to a phosphorescent layer.

The invention is described in greater detail by the following examples, without wishing to restrict it thereby. The person skilled in the art will be able to produce further electronic devices according to the invention, in particular organic electroluminescent devices, without inventive step.

EXAMPLES

The following syntheses are—unless indicated otherwise—carried out under a protective-gas atmosphere in dried solvents. The solvents and reagents can be purchased from ALDRICH or ABCR. The figures in square brackets in each case represent the CAS numbers of the starting materials known from the literature.

Example 1

2,4,6,8,10,12-Hexacyano-1,3,5,7,9,11-hexaazatriphenylene

A) 1H,3H,5H,7H,9H,11H-1,3,5,7,9,11-Hexaazatriphenylene-2,4,6,8,10,12-hexaone

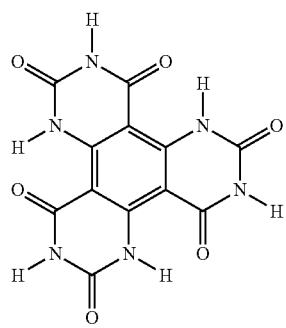 [SMILES: O=c1[nH]c(=O)c2c([nH]1)c1c(=O)[nH]c(=O)[nH]c1c1c(=O)[nH]c(=O)[nH]c21]

A melt of 148.6 g (500 mmol) of trimethyl 2,4,6-triamino-1,3,5-benzene-tricarboxylate [139286-26-3] and 450.5 g (7.5 mol) of urea are melted and heated at 200° C. until (about 4 h) the mass solidifies, with methanol and water formed being distilled off. After cooling, the mass is introduced into 2000 ml of water and comminuted with vigorous stirring. The sand-coloured solid obtained in this way is filtered off with suction and again washed by stirring with 2000 ml of water at 70° C. The solid is filtered off with suction, washed five times with 500 ml of water each time and then dried in vacuo. Yield: 125.8 g (381 mmol), 76%.

B) 2,4,6,8,10,12-Hexachloro-1,3,5,7,9,11-hexaazatriphenylene

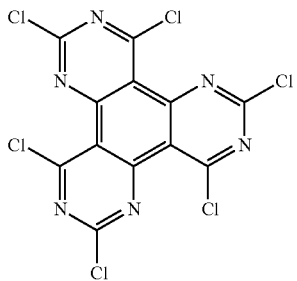 [SMILES: Clc1nc(Cl)c2c(n1)c1c(Cl)nc(Cl)nc1c1c(Cl)nc(Cl)nc21]

85 ml of N,N-dimethylaniline are added dropwise to a suspension of 33.0 g (100 mmol) of 1H,3H,5H,7H,9H,11H-1,3,5,7,9,11-hexaazatriphenylene-2,4,6,8,10,12-hexaone in 185 ml of phosphoryl chloride. The reaction mixture is heated under reflux for 20 h, then all volatile components are stripped off at 50° C. in vacuo. A mixture of 500 g of ice and 500 ml of water is added to the brown residue, and the mixture is stirred for 1 h. The brown solid is filtered off with suction, washed three times with 100 ml of water each time and then dried in vacuo. The crude product is recrystallised from acetonitrile. Yield: 26.9 g (61 mmol), 61%.

C) 2,4,6,8,10,12-Hexacyano-1,3,5,7,9,11-hexaazatriphenylene

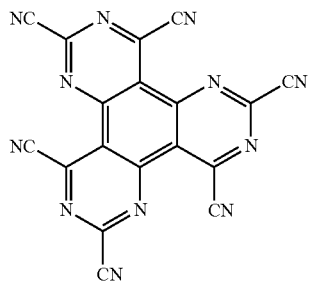 [SMILES: N#Cc1nc(C#N)c2c(n1)c1c(C#N)nc(C#N)nc1c1c(C#N)nc(C#N)nc21]

A suspension of 22.0 g (50 mmol)) of 2,4,6,8,10,12-hexachloro-1,3,5,7,9,11-hexaazatriphenylene and 26.0 g (400 mmol) of potassium cyanide in 300 ml of anhydrous acetonitrile is stirred at room temperature for 100 h. The reaction mixture is poured into a vigorously stirred mixture of 1000 g of ice and 500 ml of water, the precipitate formed is filtered off with suction, washed three times with 200 ml of water and dried in vacuo. The crude product is dissolved in 3000 ml of warm acetonitrile and eluted over aluminium oxide, acidic, activity grade 1 (400 g). After removal of the acetonitrile in vacuo, the residue is subjected to fractional sublimation twice (p about $10^{-5}$ mbar, T=380° C.). Yield: 12.3 g (32 mmol), 64%; purity: 99.9% according to HPLC.

Example 2

2,5,7,9,10,12-Hexacyano-1,3,4,6,8,11-hexaazatriphenylene

A) 4H,5H,-2,4,5,7-Tetraazaphenanthrene-1,3,6,8,9,10-hexaone

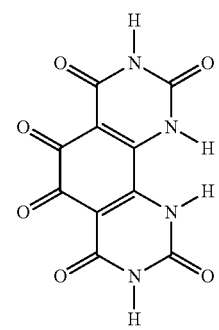 [SMILES: O=C1C(=O)c2c([nH]c(=O)[nH]c2=O)-c2[nH]c(=O)[nH]c(=O)c21]

84.0 ml (210 mmol) of n-butyllithium (2.5 molar in n-hexane) are added dropwise to a solution, cooled to −78° C., of 44.7 g (100 mmol) of 2,2',6,6'-tetrakis-tert-butoxy-4,4'-bipyrimidine [59549-56-3] in 500 ml of diethyl ether, and the mixture is stirred for a further 1 h. A solution of 11.8 g (100 mmol) of dimethyl oxalate in 100 ml of diethyl ether is then added to the reaction mixture, the reaction mixture is stirred at −78° C. for a further 30 min. and allowed to warm to 0° C., and 200 ml of 1 N ammonium chloride solution are added. After stirring at room temperature for 3 h, the organic phase is separated off, dried over magnesium sulfate, and the diethyl ether is then removed in vacuo. The oil obtained in this way is dissolved in 200 ml of THF, 20 ml of 1 N HCl are added, and the mixture is heated under reflux for 1 h. After cooling, the reaction mixture is poured onto a mixture of 500 g of ice, 300 ml of water and 13 ml of conc. ammonia solution, the precipitated solid is filtered off with suction, washed three times with water and dried in vacuo. Yield: 21.5 g (78 mmol), 78%.

B) 1,3,6,8-Tetrachloro-2,4,5,7-tetraazaphenanthrene-9,10-dione

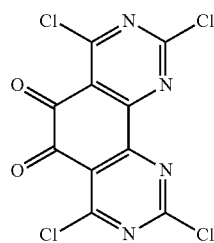 [SMILES: O=C1C(=O)c2c(Cl)nc(Cl)nc2-c2nc(Cl)nc(Cl)c21]

50 ml of N,N-dimethylaniline are added dropwise to a suspension of 13.8 g (50 mmol) of 4H,5H,-2,4,5,7-tetraazaphenanthrene-1,3,6,8,9,10-hexaone in 90 ml of phosphoryl chloride. The reaction mixture is heated under reflux for 20 h, all volatile components are then stripped off in vacuo at 50° C. 300 ml of water are added to the brown residue, and the mixture is stirred for 1 h. The brown solid is filtered off with suction, washed three times with 50 ml of water each time and then dried in vacuo. The crude product is recrystallised from acetonitrile. Yield: 9.8 g (28 mmol), 56%.

C) 1,3,6,8-Tetracyano-2,4,5,7-tetraazaphenanthrene-9,10-dione

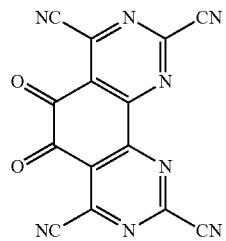 [SMILES: N#Cc1nc(C#N)c2c(n1)-c1nc(C#N)nc(C#N)c1C(=O)C2=O]

A suspension of 8.75 g (25 mmol) of 1,3,6,8-tetrachloro-2,4,5,7-tetraazaphenanthrene-9,10-dione and 9.1 g (140 mmol) of potassium cyanide in 200 ml of anhydrous acetonitrile is stirred at room temperature for 100 h. The reaction mixture is poured into a vigorously stirred mixture of 500 g of ice and 300 ml of water, the precipitate formed is filtered off with suction, washed three times with 50 ml of water and dried in vacuo. The crude product is dissolved in 2000 ml of warm acetonitrile and eluted over aluminium oxide, acidic, activity grade 1 (300 g). Yield: 5.6 g (18 mmol), 72%.

D) 2,5,7,9,10,12-Hexacyano-1,3,4,6,8,11-hexaazatriphenylene

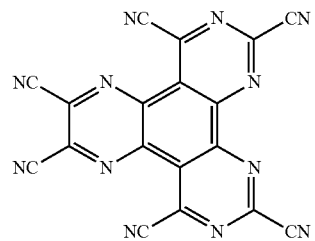 [SMILES: N#Cc1nc(C#N)c2c(n1)c1nc(C#N)nc(C#N)c1c1nc(C#N)c(C#N)nc12]

5.3 g (17 mmol) of 1,3,6,8-tetracyano-2,4,5,7-tetraazaphenanthrene-9,10-dione and 2.1 g (19 mmol) of 2,3-diaminomaleodinitrile [1187-42-4] are heated under reflux for 3 h in 250 ml of ethanol and 1 ml of glacial acetic acid. The warm reaction mixture is evaporated in vacuo until it becomes cloudy, left to stand at 0° C. overnight, the solid which has crystallised out is filtered off with suction, dissolved in 1000 ml of warm acetonitrile and eluted over aluminium oxide, acidic, activity grade 1 (100 g). After removal of the acetonitrile in vacuo, the residue is subjected to fractional sublimation twice (p about $10^{-5}$ mbar, T=380° C.). Yield: 4.2 g (11 mmol), 65%; purity: 99.9% according to HPLC.

Example 3

2,4,6,8,10,12-Hexaphenyl-1,3,5,7,9,11-hexaazatriphenylene

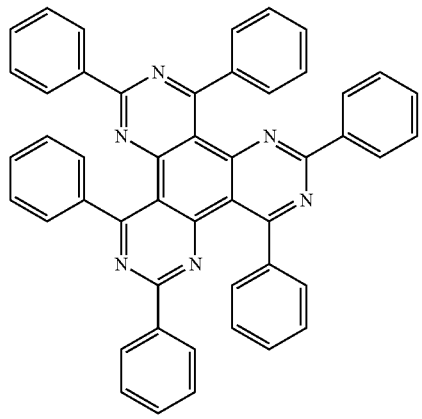 [SMILES: c1ccc(-c2nc(-c3ccccc3)c3c(n2)c2c(-c4ccccc4)nc(-c4ccccc4)nc2c2c(-c4ccccc4)nc(-c4ccccc4)nc32)cc1]

A mixture of 44.1 g (100 mmol) of 2,4,6,8,10,12-hexachloro-1,3,5,7,9,11-hexaazatriphenylene, 97.5 g (800 mmol) of phenylboronic acid, 318.48 g (1.5 mol) of tripotassium phosphate, 5.8 g (5 mmol) of tetrakistriphenylphosphinopalladium(0), 1500 ml of toluene, 200 ml of dioxane and 1000 ml of water is heated under reflux for 12 h. After cooling, the organic phase is separated off, washed twice with 1000 ml of water each time and dried over magnesium sulfate. The organic phase is evaporated to a volume of about 250 ml at 70° C. in vacuo, and 800 ml of ethanol are then added successively. After cooling, the precipitated solid is filtered off with suction, washed three times with ethanol and dried in vacuo. After recrystallisation five times from DMF, the product is subjected to fractional sublimation (p about $10^{-6}$ mbar, T=360° C.). Yield: 31.8 g (46 mmol), 46%; purity: 99.9% according to HPLC.
The following compounds are obtained analogously through the use of the corresponding boronic acids:
| Ex. | Boronic acid | Product | Yield |
|---|---|---|---|
| 4 | 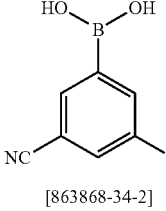 [863868-34-2] | 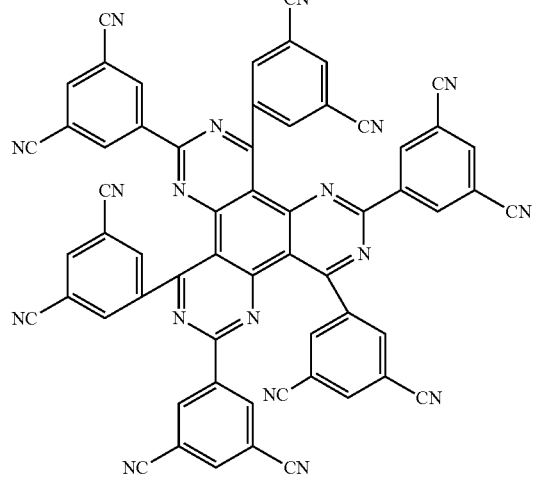 | 33% |
| 5 | 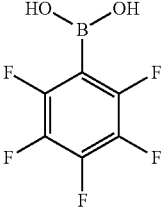 [1582-24-7] | 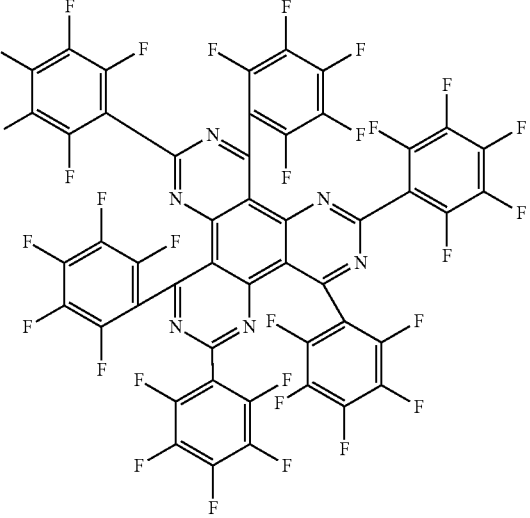 | 21% |
| 6 | 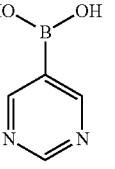 [109299-78-7] | 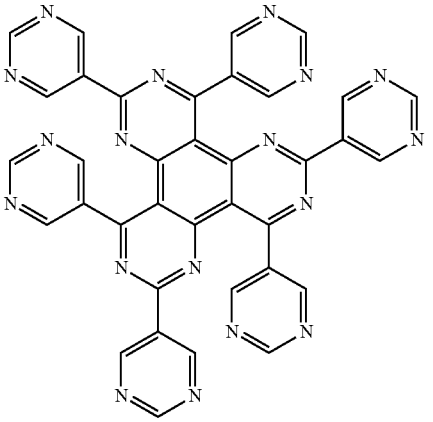 [SMILES: c1ncc(-c2nc(-c3cncnc3)c3c(n2)c2c(-c4cncnc4)nc(-c4cncnc4)nc2c2c(-c4cncnc4)nc(-c4cncnc4)nc32)cn1] | 38% |

-continued

| Ex. | Boronic acid | Product | Yield |
|---|---|---|---|
| 7 | 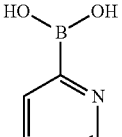
[852362-24-4] | 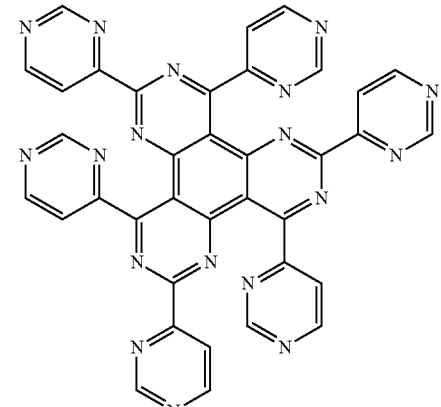 | 30% |

Example 8

2,4,6,8,10,12-Hexakis(diphenylamino)-1,3,5,7,9,11-hexaazatriphenylene

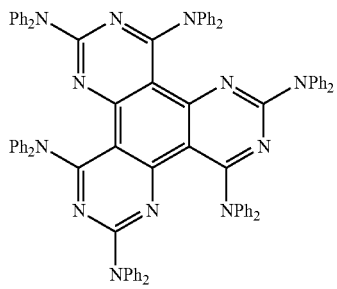

26.0 g (650 mmol) of sodium hydride (60% by weight dispersion in mineral oil) are added in portions to a mixture of 44.1 g (100 mmol) of 2,4,6,8,10,12-hexachloro-1,3,5,7,9,11-hexaazatriphenylene and 135.4 g (800 mmol) of diphenylamine in 500 ml of DMF, and the mixture is stirred at 60° C. for 8 h after the evolution of gas has subsided. After cooling, the reaction mixture is carefully poured onto a mixture of 1 kg of ice and 500 ml of water, then extracted three times with 500 ml of dichloromethane, the combined extracts are washed five times with 500 ml of water each time, and the organic phase is dried over magnesium sulfate. The organic phase is filtered through aluminium oxide, neutral, activity grade 1. After removal of the solvent, the residue is recrystallised five times from dioxane. Yield: 44.5 g (36 mmol), 36%; purity: 99.9% according to HPLC.

Example 9

Production and Characterisation of Organic Electroluminescent Devices

OLEDs according to the invention are produced by a general process in accordance with WO 2004/058911, which is adapted to the circumstances described here (layer-thickness variation, materials used).

The results for various OLEDs are presented in Examples 10 to 16 below. Glass plates coated with structured ITO (indium tin oxide) form the substrates of the OLEDs. For improved processing, 20 nm of PEDOT (applied by spin coating from water; purchased from H. C. Starck, Goslar, Germany; poly(3,4-ethylenedioxy-2,5-thiophene)) is applied to the substrate. The OLEDs consist of the following layer sequence: substrate/PEDOT 20 nm/hole-injection layer (HIL) 5 nm/hole-transport layer (HTL-1) 20 nm/hole-transport layer (HTL-2) 20 nm/emission layer (EML) 30 nm/electron-transport layer (ETL) 20 nm and finally a cathode.

The materials apart from PEDOT are applied by thermal vapour deposition in a vacuum chamber. The emission layer here always consists of a matrix material (host) and a dopant, which is admixed with the host by co-evaporation. The matrix material used in Examples 10 to 16 described below is compound H1, that used in Examples 17 to 19 is compound H2, each of which is doped with 10% of D1 or the phosphorescent dopant D2. These OLEDs exhibit green emission. The hole-transport material used in HTL-1 is compound HTM-1. The hole-transport material used in HTL-2 is NPB. The cathode in Examples 10 to 16 is formed by an LiF layer having a thickness of 1 nm and an Al layer having a thickness of 100 nm deposited on top and that in Examples 17 to 19 is formed by an Al layer having a thickness of 100 nm. Table 1 shows the chemical structures of the materials used to build up the OLEDs.

These OLEDs are characterised by standard methods; for this purpose, the electroluminescence spectra, the efficiency (measured in cd/A) as a function of the luminance, calculated from current/voltage/luminance characteristic lines (IUL characteristic lines), and the lifetime are determined. The lifetime is defined as the time after which the initial luminance of 25,000 cd/m$^2$ or 8000 cd/m$^2$ has dropped to half. The use voltage is defined as the voltage at which the OLED achieves a luminance of 1 cd/m$^2$.

Table 2 summarises the results for some OLEDs. The hole-injection material used in accordance with the invention in the hole-injection layer (HIL) is HIM-1 (2,4,6,8,10,12-hexacyano-1,3,5,7,9,11-hexaazatriphenylene, from Example 1), HIM-2 (2,5,7,9,10,12-hexacyano-1,3,4,6,8,11-hexaazatriphenylene) or HIM-3 (in accordance with the prior art). Compared with the prior art, OLEDs which comprise HIM-1 or HIM-2 in the hole-injection layer are distinguished by improved efficiency, in particular improved power efficiency, and lifetime compared with HIM-3 in accordance with the prior art.

The electron-transport material employed in the electron-transport layer (ETL) is either AlQ$_3$ in accordance with the prior art or a co-evaporated combination of ETM-3 (50%) and ETM-4 (50%) or in accordance with the invention 2,4,6,8,10,12-hexaphenyl-1,3,5,7,9,11-hexaazatriphenylene (ETM-1, in accordance with Example 3) or 2,4,6,8,10,12-hexa(5-pyrimidinyl)-1,3,5,7,9,11-hexaazatriphenylene (ETM-2, in accordance with Example 6).

TABLE 1

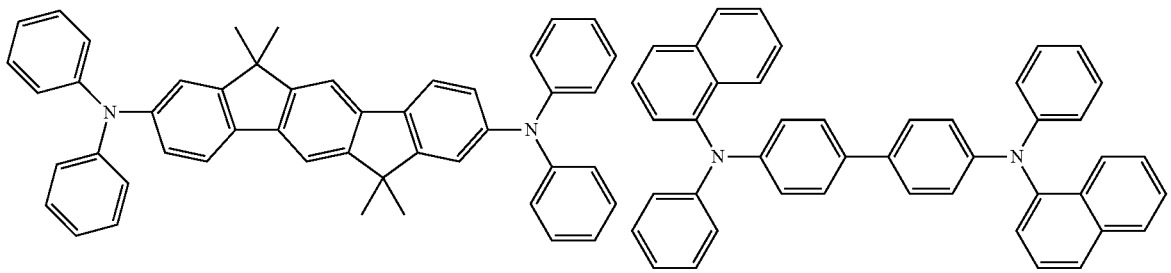

HTM-1 NPB

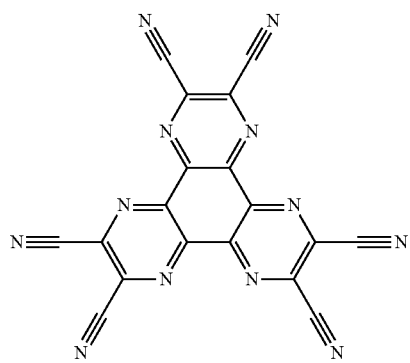 [SMILES: N#Cc1nc2c3nc(C#N)c(C#N)nc3c3nc(C#N)c(C#N)nc3c2nc1C#N] 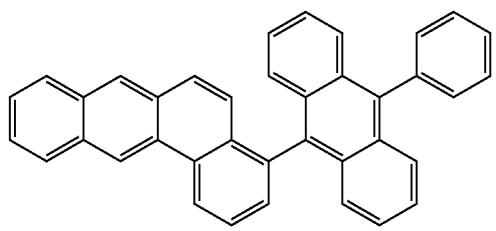 [SMILES: c1ccc(-c2c3ccccc3c(-c3cccc4c3ccc3cc5ccccc5cc34)c3ccccc23)cc1]

HIM-3 (prior art) H1

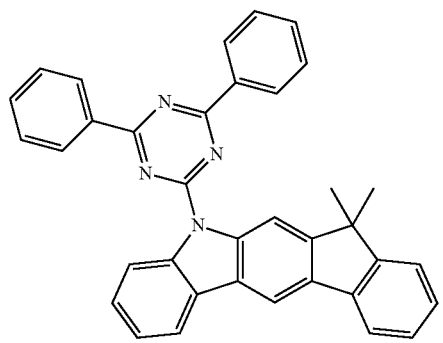 [SMILES: CC1(C)c2ccccc2-c2cc3c4ccccc4n(-c4nc(-c5ccccc5)nc(-c5ccccc5)n4)c3cc21] 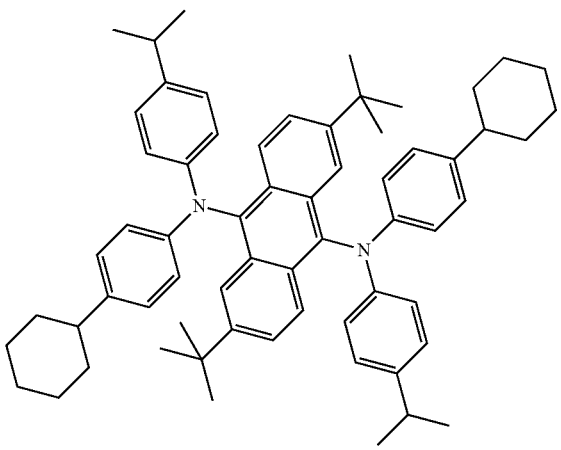 [SMILES: CC(C)c1ccc(N(c2ccc(C3CCCCC3)cc2)c2c3ccc(C(C)(C)C)cc3c(N(c3ccc(C(C)C)cc3)c3ccc(C4CCCCC4)cc3)c3ccc(C(C)(C)C)cc23)cc1]

H2 D1

TABLE 1-continued

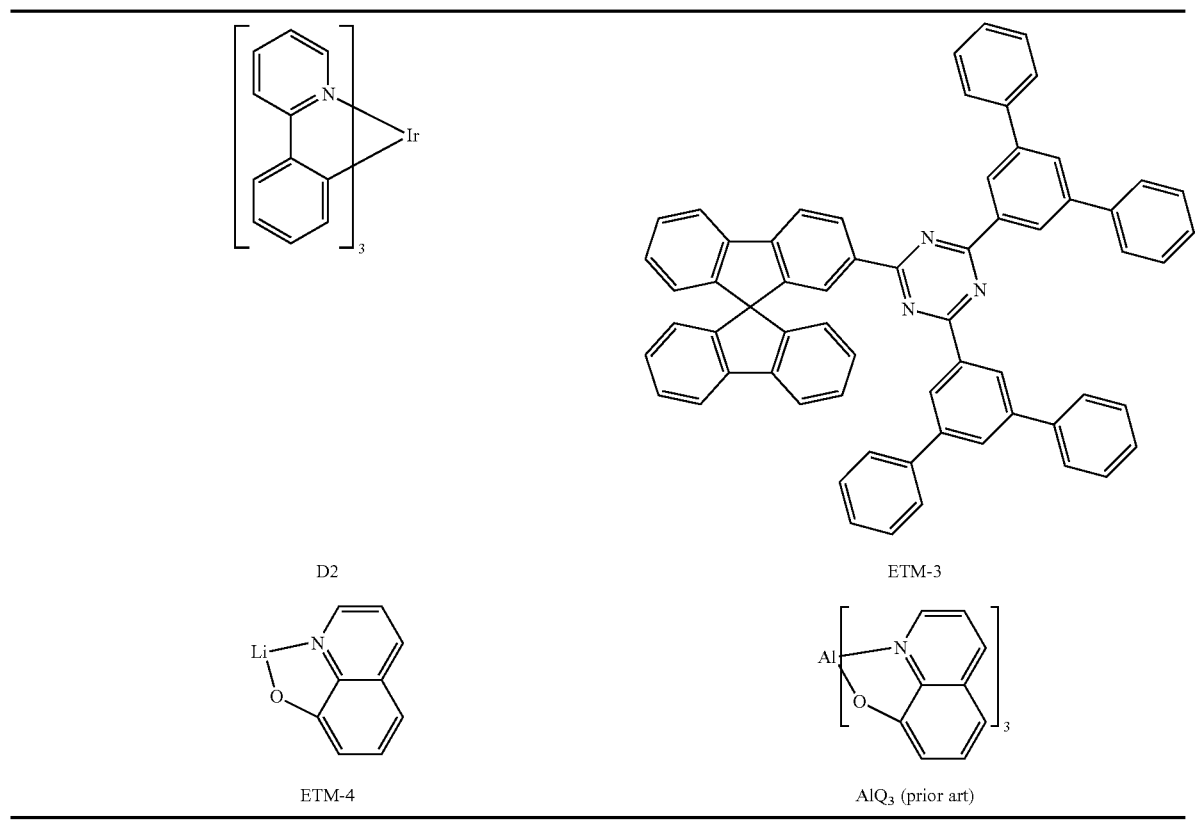

D2

ETM-3

ETM-4

AlQ₃ (prior art)

TABLE 2

| Ex. | HIL | ETL | Use voltage | Voltage for 1000 cd/m² | Efficiency at 1000 cd/m² | CIE x/y at 1000 cd/m² | Lifetime for 25000 cd/m² |
|---|---|---|---|---|---|---|---|
| 10 | HIM-1 | AlQ₃ | 2.7 V | 4.8 V | 18.9 cd/A | 0.34/0.63 | 410 h |
| 11 | HIM-2 | AlQ₃ | 2.7 V | 4.8 V | 18.5 cd/A | 0.34/0.63 | 400 h |
| 12 (comp.) | HIM-3 | AlQ₃ | 2.8 V | 5.0 V | 17.1 cd/A | 0.34/0.62 | 355 h |
| 13 | HIM-1 | ETM-1 | 2.7 V | 5.0 V | 19.0 cd/A | 0.33/0.64 | 465 h |
| 14 | HIM-1 | ETM-2 | 2.7 V | 4.8 V | 21.5 cd/A | 0.33/0.63 | 450 h |
| 15 | HIM-2 | ETM-1 | 2.8 V | 5.0 V | 18.7 cd/A | 0.34/0.62 | 400 h |
| 16 | HIM-2 | ETM-2 | 2.7 V | 4.7 V | 20.1 cd/A | 0.34/0.63 | 435 h |
| 17 (comp.) | HIM-3 | ETM-3 ETM-4 | 2.9 V | 4.5 V | 36.7 | 0.33/0.63 | 430 h 8000 cd/m² |
| 18 | HIM-1 | ETM-3 ETM-4 | 2.6 V | 4.0 V | 43.3 | 0.33/0.63 | 500 h 8000 cd/m² |
| 19 | HIM-2 | ETM-3 ETM-4 | 2.4 V | 3.8 V | 46.0 | 0.33/0.63/ | 540 h 8000 cd/m² |

The invention claimed is:
1. A compound of the formula (2) and (5),

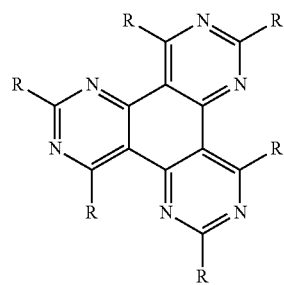

formula (2)

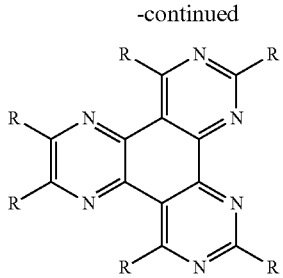

formula (5)

where the following applies to the symbols used:

R is on each occurrence, identically, H, D, F, Cl, Br, I, CHO, N(R¹)₂, N(Ar)₂, C(=O)R¹, C(=O)Ar, P(=O)

$(R^1)_2$, $F(=O)(Ar)_2$, $S(=O)Ar$, $S(=O)_2Ar$, $CR^1=CR^1Ar$, CN, $NO_2$, $Si(R^1)_3$, $B(OR^1)_2$, $B(R^1)_2$, $B(Ar)_2$, $B(N(R^1)_2)_2$, $P(R^1)_2$, $OSO_2R^1$, COOH, $COOR^1$, a straight-chain alkyl, alkoxy or thioalkoxy group having 1 to 40 C atoms or a straight-chain alkenyl or alkynyl group having 2 to 40 C atoms or a branched or cyclic alkyl, alkenyl, alkynyl, alkoxy or thioalkoxy group having 3 to 40 C atoms, each of which is optionally substituted by one or more radicals $R^1$, where one or more non-adjacent $CH_2$ groups is optionally replaced by $R^1C=CR^1$, $C\equiv C$, $Si(R^1)_2$, $Ge(R^1)_2$, $Sn(R^1)_2$, $C=O$, $C=S$, $C=Se$, $C=NR^1$, $P(=O)(R^1)$, SO, $SO_2$, $NR^1$, O, S or $CONR^1$ and where one or more H atoms is optionally replaced by D, F, Cl, Br, I, CN or $NO_2$, or an aromatic or heteroaromatic ring system having 5 to 60 aromatic ring atoms, which may in each case be substituted by one or more radicals $R^1$, or an aryloxy or heteroaryloxy group having 5 to 60 aromatic ring atoms, which may in each case be substituted by one or more radicals $R^1$, or a combination of these systems; two adjacent radicals R here may in each case form a mono- or polycyclic, aliphatic, aromatic or heteroaromatic ring system with one another;

$R^1$ is on each occurrence, identically or differently, H, D, F, Cl, Br, I, CHO, $N(R^2)_2$, $N(Ar)_2$, $C(=O)Ar$, $P(=O)(Ar)_2$, $S(=O)Ar$, $S(=O)_2Ar$, $CR^2=CR^2Ar$, CN, $NO_2$, $Si(R^2)_3$, $B(OR^2)_2$, $B(R^2)_2$, $B(N(R^2)_2)_2$, $OSO_2R^2$, a straight-chain alkyl, alkoxy or thioalkoxy group having 1 to 40 C atoms or a straight-chain alkenyl or alkynyl group having 2 to 40 C atoms or a branched or cyclic alkyl, alkenyl, alkynyl, alkoxy or thioalkoxy group having 3 to 40 C atoms, each of which is optionally substituted by one or more radicals $R^2$, where one or more non-adjacent $CH_2$ groups is optionally replaced by $R^2C=CR^2$, $C\equiv C$, $Si(R^2)_2$, $Ge(R^2)_2$, $Sn(R^2)_2$, $C=O$, $C=S$, $C=Se$, $C=NR^2$, $P(=O)(R^2)$, SO, $SO_2$, $NR^2$, O, S or $CONR^2$ and where one or more H atoms is optionally replaced by D, F, Cl, Br, I, CN or $NO_2$, or an aromatic or heteroaromatic ring system having 5 to 60 aromatic ring atoms, which may in each case be substituted by one or more radicals $R^2$, or an aryloxy or heteroaryloxy group having 5 to 60 aromatic ring atoms, which is optionally substituted by one or more radicals $R^2$, or a combination of these systems;

Ar is on each occurrence, identically or differently, an aromatic or heteroaromatic ring system having 5 to 30 aromatic ring atoms, which is optionally substituted by one or more non-aromatic radicals $R^1$; two radicals Ar which are bonded to the same nitrogen or phosphorus atom may also be linked to one another here by a single bond or a bridge selected from the group consisting of $B(R^2)$, $C(R^2)_2$, $Si(R^2)_2$, $C=O$, $C=NR^2$, $C=C(R^2)_2$, O, S, $S=O$, $SO_2$, $N(R^2)$, $P(R^2)$ and $P(=O)R^2$;

$R^2$ is on each occurrence, identically or differently, H, D or an aliphatic, aromatic and/or heteroaromatic hydrocarbon radical having 1 to 20 C atoms, in which, in addition, H atoms is optionally replaced by F; two or more adjacent substituents $R^2$ here may also form a mono- or polycyclic, aliphatic or aromatic ring system with one another.

2. The compound according to claim 1 wherein the heteroaromatic skeleton has C3h or C2v symmetry.

3. The compound according to claim 1 wherein R stands, identically on each occurrence, for H, F, $C(=O)Ar$, $P(=O)(Ar)_2$, CN, a straight-chain alkyl group having 1 to 10 C atoms or a branched or cyclic alkyl group having 3 to 10 C atoms, each of which is optionally substituted by one or more radicals $R^1$, where one or more H atoms is optionally replaced by F or CN, or an aromatic or heteroaromatic ring system having 5 to 40 aromatic ring atoms, which may in each case be substituted by one or more radicals $R^1$.

4. An organic electroluminescent device which comprises the compound according to claim 1 is employed as electron-transport material or as hole-blocking material in an electron-transport layer or in a hole-blocking layer and/or in that the compound according to claim 1 is employed as charge-generation material in a charge-generation layer and/or in that the compound according to claim 1 is employed as matrix material for an emitting compound for a phosphorescent compound.

5. The compound according to claim 1 wherein R is on each occurrence, identically, H, F, $N(Ar)_2$, CN, or an aromatic or heteroaromatic ring system having 5 to 60 aromatic ring atoms, which may in each case be substituted by one or more radicals $R^1$.

6. The compound according to claim 1 wherein R is on each occurrence, identically, F, $N(Ar)_2$, CN, or an aromatic or heteroaromatic ring system having 5 to 60 aromatic ring atoms, which may in each case be substituted by one or more radicals $R^1$.

7. A process for the preparation of the compound according to claim 1, which comprises the following reaction steps:
   a) synthesizing the corresponding halogenated skeleton; and
   b) conversion of the halogen into the substituent.

8. An oligomer, polymer or dendrimer containing one or more compounds according to claim 1, where one or more radicals R represent bonds from the compound to the polymer, oligomer or dendrimer.

9. An electronic device comprising the compound according to claim 1.

10. The electronic device as claimed in claim 9, wherein the device is selected from the group consisting of an organic electroluminescent device, an organic integrated circuit, an organic field-effect transistor, an organic thin-film transistor, an organic light-emitting transistor, an organic solar cell, a dye-sensitised solar cell, an organic optical detector, an organic photoreceptor, an organic field-quench device, a light-emitting electrochemical cell, an organic laser diode and an organic plasmon emitting device.

11. An organic electroluminescent device which comprises the compound according to claim 1 is used in a hole-injection or hole-transport layer.

12. An organic electroluminescent device which comprises one of the following structures a) or b):
   a) anode-hole-injection layer comprising at least one compound according to claim 1 hole-transport layer-emitting layer-cathode;
   or
   b) anode-hole-injection layer-hole-transport layer comprising at least one compound according to claim 1 hole-transport layer-emitting layer-cathode,
   where the electroluminescent device may also comprise further layers in addition to the said layers.

13. An organic electroluminescent device which comprises the compound according to claim 1 is employed as electron-transport material or as hole-blocking material in an electron-transport layer or in a hole-blocking layer and/or in that the compound according to claim 1 is employed as charge-generation material in a charge-generation layer and/or in that the compound according to claim 1 is employed as matrix material for an emitting compound.

* * * * *